United States Patent
Leng

(10) Patent No.: US 10,150,987 B2
(45) Date of Patent: Dec. 11, 2018

(54) LABELED CIRCULAR DNA MOLECULES FOR ANALYSIS OF DNA TOPOLOGY, AND TOPOISOMERASES AND FOR DRUG SCREENING

(71) Applicant: Fenfei Leng, Palmetto Bay, FL (US)

(72) Inventor: Fenfei Leng, Palmetto Bay, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/857,056

(22) Filed: Dec. 28, 2017

(65) Prior Publication Data

US 2018/0135112 A1  May 17, 2018

Related U.S. Application Data

(63) Continuation of application No. 15/286,046, filed on Oct. 5, 2016, now Pat. No. 9,890,416.

(60) Provisional application No. 62/237,236, filed on Oct. 5, 2015.

(51) Int. Cl.
  *C12Q 1/68* (2018.01)
  *C07H 21/00* (2006.01)
  *C12Q 1/6818* (2018.01)

(52) U.S. Cl.
  CPC ............ *C12Q 1/6818* (2013.01); *C07H 21/00* (2013.01)

(58) Field of Classification Search
  CPC .................................. C12Q 1/68; C07H 21/00
  See application file for complete search history.

(56) References Cited

U.S. PATENT DOCUMENTS

| | | |
|---|---|---|
| 5,468,610 A | 11/1995 | Polymeropoulos et al. |
| 2001/0053519 A1 | 12/2001 | Fodor et al. |
| 2007/0178456 A1 | 8/2007 | Trotta |
| 2008/0020973 A1 | 1/2008 | Stivers et al. |
| 2008/0131878 A1 | 6/2008 | Latham et al. |
| 2011/0207132 A1 | 8/2011 | Sintim |
| 2012/0225788 A1 | 9/2012 | Madrid et al. |
| 2013/0090300 A1 | 4/2013 | Bauman et al. |
| 2014/0112871 A1 | 4/2014 | Basnakian et al. |
| 2015/0322022 A1 | 11/2015 | LaVoie et al. |

OTHER PUBLICATIONS

Roychoudhury et al. [J. of Biomolecular Screening 8 (2) 15722 (Year: 2003)].*

Frith, M. C., "A new repeat-masking method enables specific detection of homologous sequences." Nucleic Acids Research, 2011, 39 (4): 2-8.

Greaves, D.R. et al., "Facile cruciform formation by an (A-T)34 sequence from a Xenopus globin gene." Journal of Molecular Biology, Oct. 1985, 185 (3): Abstract.

Gu, M. et al., "Fluorescently labeled circular DNA molecules for DNA topology and topoisomerases." Scientific Reports, Oct. 2016, 6: 36006. doi: 10.1038/srep36006.

Holland, P. M. et al., "Detection of specific polymerase chain reaction product by utilizing the 5'→ 3' exonuclease activity of Thermus aquaticus DNA polymerase." Proc. Natl. Acad. Sci., Aug. 1991, 88: 7276-7280.

Jude, K.M. et al., "Real-time detection of DNA topological changes with a fluorescently labeled cruciform." Nucleic Acids Research., May 2013, 41(13): 1-9, e133. doi:10.1093/nar/gkt413.

Leng, F. et al., "Dividing a supercoiled DNA molecule into two independent topological domains." PNAS, Dec. 2011, 108 (50): 19973-19978.

Leng, F., "DNA Bending by Proteins: Utilizing Plasmid pBendAT as a Tool." Methods in Molecular Biology, 1054 (chapter 18): 2013, 1054: 264-282.

Leng, F., McMacken, R., "Potent stimulation of transcription-coupled DNA supercoiling by sequence-specific DNA-binding proteins." PNAS, Jul. 2002, 99 (14): 9139-9144.

Maxwell, A. et al., "High-throughput assays for DNA gyrase and other topoisomerases." Nucleic Acids Research, Aug. 2006, 34(15): 1-7, e104. doi:10.1093/nar/gk1504.

Ponte, I. et al, "Narrow A/T-rich zones present at the distal 5'-flanking sequences of the zein genes Zc1 and Zc2 bind a unique 30 kDa HMG-like protein." Plant Molecular Biology, 1994, 26: 1893-1906.

Ranjan, N. et al., "Selective inhibition of bacterial topoisomerase I by alkynyl-bisbenzimidazoles." Med. Chem. Commun., 2014, 5: 816-825.

Roychoudhury, S. et al., "Development and Use of a High-Throughput Bacterial DNA Gyrase Assay to Identify Mammalian Topoisomerase II Inhibitors with Whole-Cell Anticancer Activity." Journal of Biomolecular Screening, 2003, 8(2): 157-163.

Samul, R., Leng, F., "Transcription-coupled Hypernegative Supervoiling of Plasmid DNA by T7 RNA Polymerase in *Escherichia coli* Topoisomerase I-Deficient Strains." J. Mol. Biol., 2007, 374: 925-935.

Shapiro, A. et al., "A homogeneous, High-Throughput Fluorescence Anisotropy-Based DNA Supercoiling Assay." Journal of Biomolecular Screening, 2010, 15(9): 1088-1098.

Yu, B., Hinchcliffe, M., "In Silico Tools for Gene Discovery." Methods in Molecular Biology, Humana Press, 2011 (Chapter 1): 1-7.

* cited by examiner

*Primary Examiner* — Ethan C Whisenant

(74) *Attorney, Agent, or Firm* — Saliwanchik, Lloyd & Eisenschenk

(57) ABSTRACT

The present invention provides labeled circular plasmid DNA molecules for studying DNA topology and topoisomerases. The molecules of the present invention also provide tools for high throughput drug screening for inhibitors of DNA gyrases and DNA topoisomerases for anticancer drug discovery and antibiotics discovery.

11 Claims, 18 Drawing Sheets

Specification includes a Sequence Listing.

FL905
5'——————ATATATA[Dab-dT]ATAT(AT)₈ATATA[Fl-dT]ATATATAT——————3'
FIG. 2
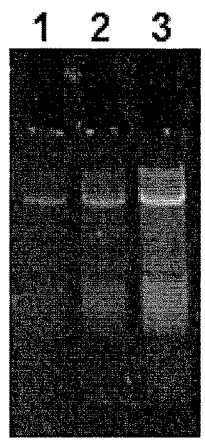 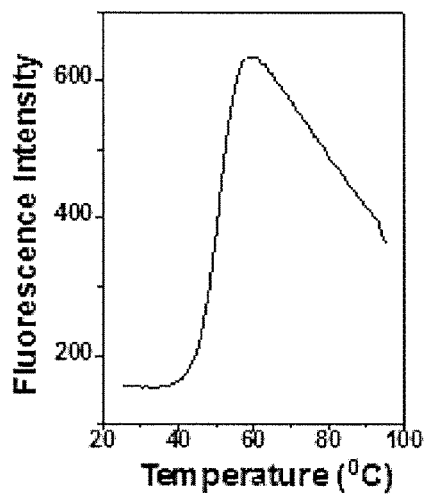
FIG. 3A    FIG. 3B
FL_AT42
```
            ↓                                                              ↓
     CCCTCAGCCCGACAGCACGAGACG(AT)₂₁GGGCCAACCAACCAGCCCCTCAGC
     GTACGGGAGTCGGGCTGTCGTGCTCTGC(TA)₂₁CCCGGTTGGTTGGTCGGGGAGTCGCCTAG
       Nt.BbvCI                                                     Nt.BbvCI
```
FIG. 3C

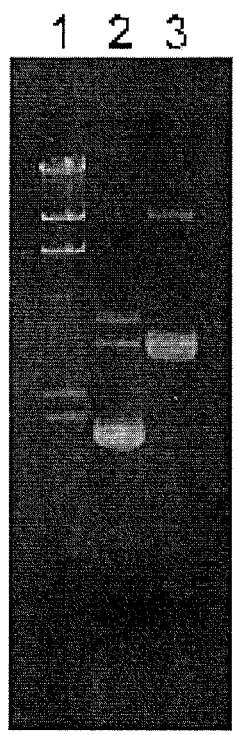 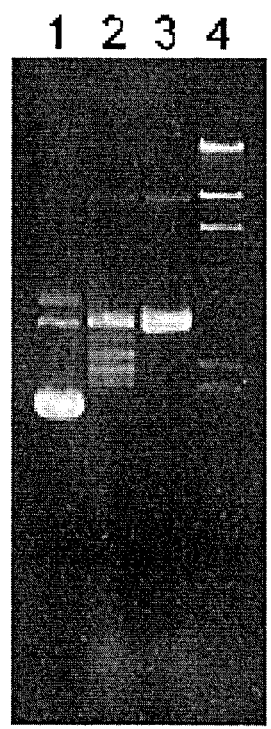 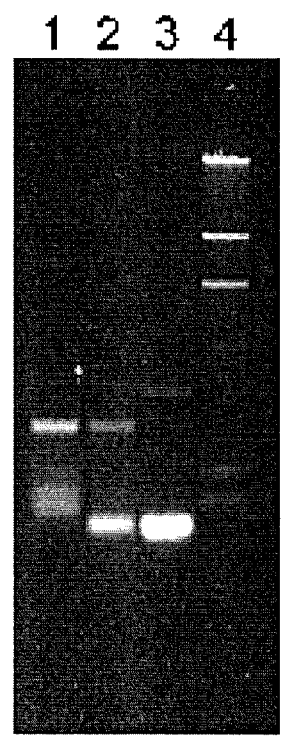
FIG. 14A    FIG. 14B    FIG. 14C
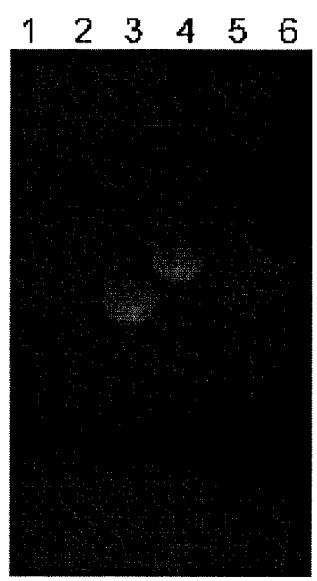 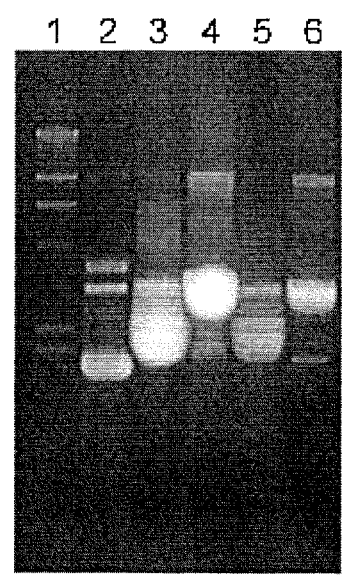
FIG. 14D    FIG. 14E

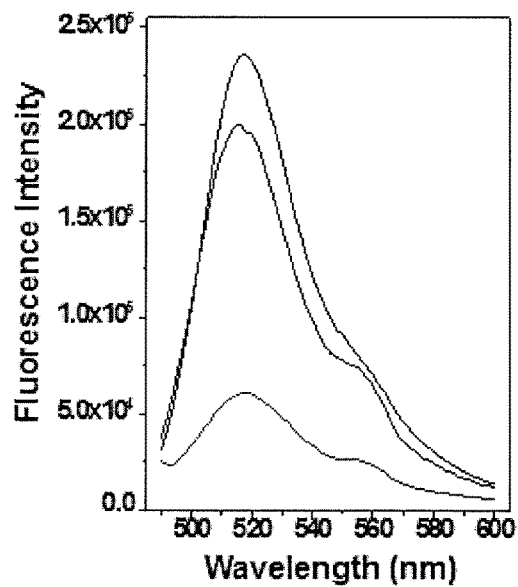
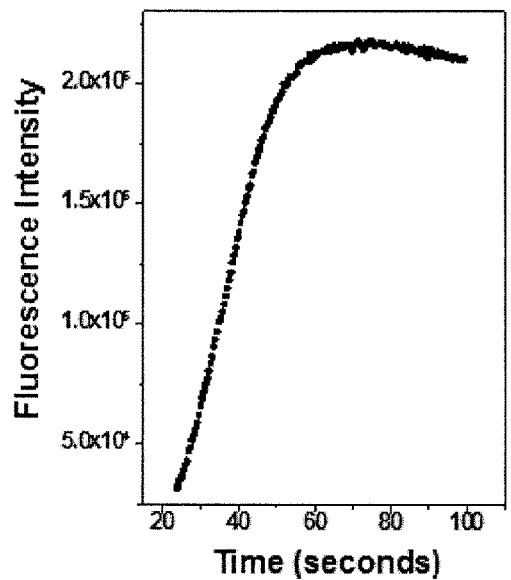
FIG. 15AFIG. 15B
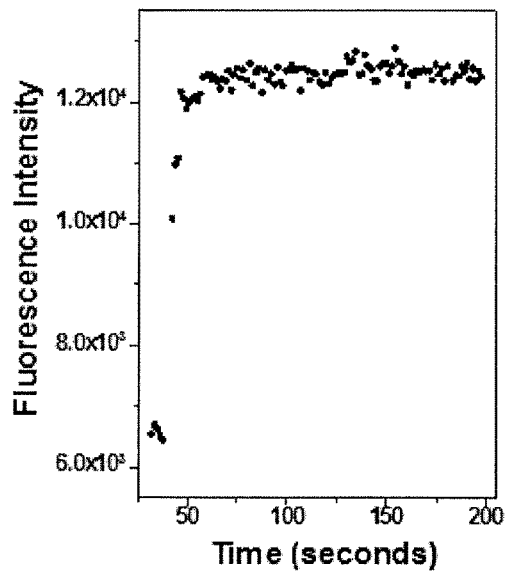
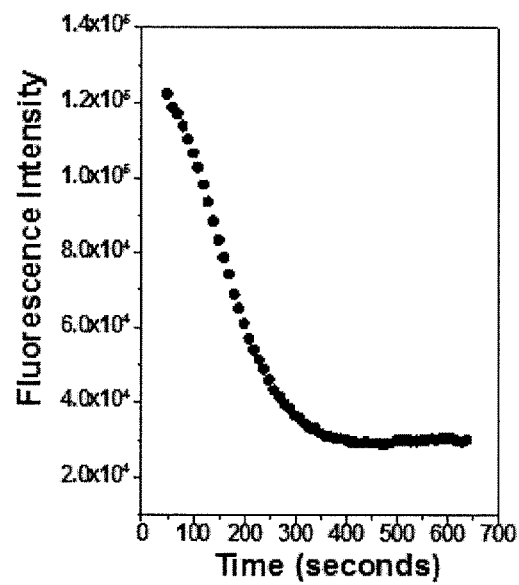
FIG. 15CFIG. 15D

FL924
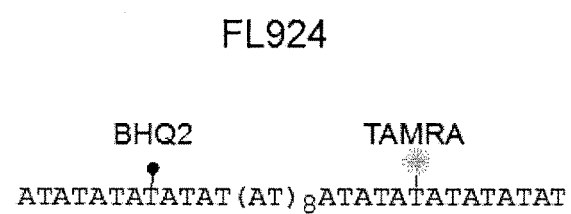
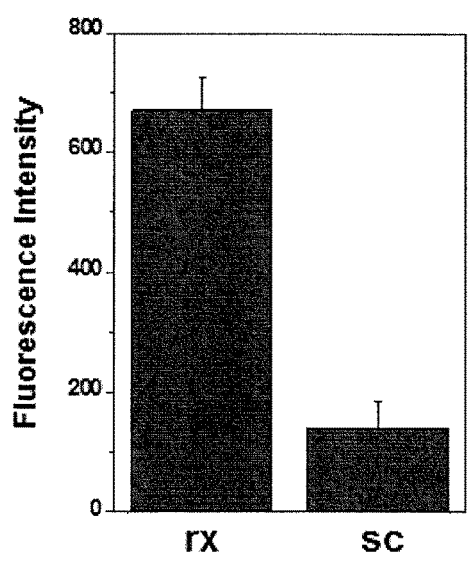
FIG. 17A
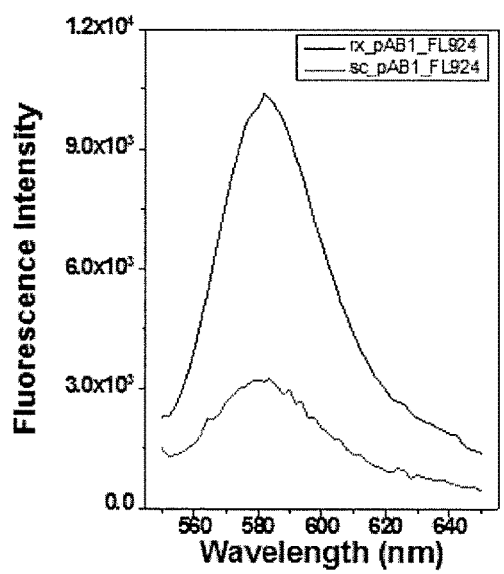
FIG. 17B

SEQUENCE LISTING

<160> NUMBER OF SEQ ID NOS: 8

<210> SEQ ID NO 1
<211> LENGTH: 90
<212> TYPE: DNA
<213> ORGANISM: Artificial
<220> FEATURE:
<223> OTHER INFORMATION: first strand of the double-stranded oligomer
      FL-AT42

<400> SEQUENCE: 1
ccctcagccc gacagcacga gacgatatat atatatatat atatatatat atatatat      60 atatgggc caaccaacca gcccctcagc                                       90

<210> SEQ ID NO 2
<211> LENGTH: 99
<212> TYPE: DNA
<213> ORGANISM: Artificial
<220> FEATURE:
<223> OTHER INFORMATION: second strand of the double-stranded oligomer
      FL-AT42

```
<400> SEQUENCE: 2
gtacgggagt cgggctgtcg tgctctgcta tatatatata tatatatata tatatatata    60
tatatatata cccggttggt tggtcgggga gtcgcctag                            99

<210> SEQ ID NO 3
<211> LENGTH: 91
<212> TYPE: DNA
<213> ORGANISM: Artificial
<220> FEATURE:
<223> OTHER INFORMATION: synthetic oligonucleotide FL882

<400> SEQUENCE: 3
ccctcagccc gacagcacga gacgatatat atatatatat atatatatat atatatatat    60
atatatgggc caaccaacca gcccctcagc g                                   91

<210> SEQ ID NO 4
<211> LENGTH: 99
<212> TYPE: DNA
<213> ORGANISM: Artificial
<220> FEATURE:
<223> OTHER INFORMATION: synthetic oligonucleotide FL883

<400> SEQUENCE: 4
gatccgctga ggggctggtt ggttggccca tatatatata tatatatata tatatatata    60
tatatatata tcgtctcgtg ctgtcgggct gagggcatg                           99

<210> SEQ ID NO 5
<211> LENGTH: 82
<212> TYPE: DNA
<213> ORGANISM: Artificial
<220> FEATURE:
<223> OTHER INFORMATION: synthetic oligonucleotide FL905
<220> FEATURE:
<221> NAME/KEY: misc_feature
<222> LOCATION: (29)..(29)
<223> OTHER INFORMATION: n represents dabcyl-dT
<220> FEATURE:
<221> NAME/KEY: misc_feature
<222> LOCATION: (55)..(55)
<223> OTHER INFORMATION: n represents fluorescein-dT

<400> SEQUENCE: 5
tcagcccgac agcacgagac gatatatana tatatatata tatatatata tatanatata    60
tatgggccaa ccaaccagcc cc                                             82

<210> SEQ ID NO 6
<211> LENGTH: 82
<212> TYPE: DNA
<213> ORGANISM: Artificial
<220> FEATURE:
<223> OTHER INFORMATION: synthetic oligonucleotide FL919
<220> FEATURE:
<221> NAME/KEY: misc_feature
<222> LOCATION: (27)..(27)
<223> OTHER INFORMATION: n represents dabcyl-dT
<220> FEATURE:
<221> NAME/KEY: misc_feature
<222> LOCATION: (57)..(57)
<223> OTHER INFORMATION: n represents fluorescein-dT

<400> SEQUENCE: 6
tcagcccgac agcacgagac gatatanata tatatatata tatatatata tatatanata    60
tatgggccaa ccaaccagcc cc                                             82
```

```
<210> SEQ ID NO 7
<211> LENGTH: 82
<212> TYPE: DNA
<213> ORGANISM: Artificial
<220> FEATURE:
<223> OTHER INFORMATION: synthetic oligonucleotide FL920
<220> FEATURE:
<221> NAME/KEY: misc_feature
<222> LOCATION: (31)..(31)
<223> OTHER INFORMATION: n represents dabcyl-dT
<220> FEATURE:
<221> NAME/KEY: misc_feature
<222> LOCATION: (53)..(53)
<223> OTHER INFORMATION: n represents fluorescein-dT

<400> SEQUENCE: 7
tcagcccgac agcacgagac gatatatata natatatata tatatatata tanatatata      60
tatgggccaa ccaaccagcc cc                                               82

<210> SEQ ID NO 8
<211> LENGTH: 82
<212> TYPE: DNA
<213> ORGANISM: Artificial
<220> FEATURE:
<223> OTHER INFORMATION: synthetic oligonucleotide FL924
<220> FEATURE:
<221> NAME/KEY: misc_feature
<222> LOCATION: (29)..(29)
<223> OTHER INFORMATION: n represents BHQ2-dT
<220> FEATURE:
<221> NAME/KEY: misc_feature
<222> LOCATION: (55)..(55)
<223> OTHER INFORMATION: n represents TAMRA-dT

<400> SEQUENCE: 8
tcagcccgac agcacgagac gatatatana tatatatata tatatatata tatanatata      60
tatgggccaa ccaaccagcc cc                                               82
```

LABELED CIRCULAR DNA MOLECULES FOR ANALYSIS OF DNA TOPOLOGY, AND TOPOISOMERASES AND FOR DRUG SCREENING

CROSS-REFERENCE TO A RELATED APPLICATION

This application is a continuation application of U.S. Ser. No. 15/286,046, filed Oct. 5, 2016, which claims the priority benefit of U.S. provisional application Ser. No. 62/237,236, filed Oct. 5, 2015, both of which are incorporated herein by reference in their entirety.

The Sequence Listing for this application is labeled "SeqList-29Sep16.txt", which was created on Sep. 29, 2016, and is 4 KB. The entire content is incorporated herein by reference in its entirety.

BACKGROUND OF THE INVENTION

DNA topology plays essential roles in several fundamental biological processes, such as DNA replication, recombination, and transcription. DNA topology is a tightly-regulated property of the DNA double helix that affects genomic stability and influences susceptibility to cancer and certain hereditary diseases, such as fragile X syndrome and autism. DNA topoisomerases that control DNA topology inside cells are important targets of anti-cancer drugs, such as camptothecin and doxorubicin, and antibacterial agents, such as ciprofloxacin.

Typically agarose gel electrophoresis is employed to study DNA topology. Because gel electrophoresis is time-consuming and labor intensive, it is desirable to develop other methods, such as fluorescence-based methods, for such studies. For example, fluorescence dyes, such as PicoGreen (1), have been shown to differentially bind to supercoiled (sc) and relaxed (rx) DNA molecules to yield different fluorescence properties. These fluorescence dyes were used to study DNA topoisomerases; however, the difference of the fluorescence intensity of the dyes binding to sc and rx DNA is too small to be widely used to study the properties of DNA topoisomerases and to screen inhibitors against these topoisomerases (1).

Another type of assay was developed based on a unique property of sc DNA molecules that prefer binding to triplex-form oligomers if the sc plasmids contain one or multiple triplex-forming sequences (2, 3). Maxwell and coworkers utilized a method in which an immobilized triplex-forming oligomer more efficiently captured sc plasmids than rx plasmids (2). The captured plasmids could subsequently be quantified by a DNA-binding dye, such as SYBR Green. However, this method requires immobilization of oligomer to a solid surface, filtration, and multiple washing steps. Because streptavidin-coated 1526-well plates are not commercially available, this method is not compatible with ultra-high throughput screening to identify gyrase inhibitors from small compound libraries using 1526-well plates.

Another method, also based on the triplex-forming oligomers, was developed by using fluorescence anisotropy for the readout (3). Nevertheless, the signal to noise ratio is a concern and an expensive fluorimeter with the capacity to measure fluorescence anisotropy is required (3).

More recently, Berger and coworkers made a circular plasmid DNA template that contains a fluorophore (fluorescein) and quencher (dabcyl) on opposite strands of a double-stranded DNA molecule and developed a real-time assay to study DNA topological changes with this fluorescently labeled DNA (4). However, the production involving two steps of fluorophore and quencher insertion into the DNA result in a low yield of fluorescently labeled DNA, which low yield is cost prohibitive and impedes wide use of the assay to study DNA topology, topoisomerases, and to screen compounds against DNA topoisomerases (4).

BRIEF SUMMARY OF THE INVENTION

Provided herein are new reagents and methods to mass-produce fluorescently labeled circular DNA molecules with high yields to study DNA topology and topoisomerases by fluorescence resonance energy transfer (FRET), and to screen anti-cancer drugs and antibiotics targeting DNA topoisomerases using high throughput drug screening.

Reagents provided include novel nucleic acid sequences comprising an adenosine-thymidine dinucleotide repeat $(AT)_n$ sequence comprising at least one fluorophore and at least one quencher, each conjugated to a deoxythymidine (dT), wherein the fluorophore-conjugated dT and the quencher-conjugated dT are separated by at least 14 nucleotides. The novel nucleic acid sequences provide superior detection efficiency and facilitate use in high throughput screening.

The subject invention further provides methods for mass-production of fluorescently labeled circular DNA molecules with high yields sufficient to study DNA topology and topoisomerases by fluorescence resonance energy transfer (FRET) and in high throughput screening to identify novel anti-cancer drugs and antibiotics targeting DNA topoisomerases.

Further provided herein are methods for screening for inhibitors targeting DNA topoisomerases, DNA gyrases, DNA nicking endonuclease, DNA endonucleases, and RNAses using the circular plasmid DNA molecules and kits for screening for said inhibitors.

The methods, molecules and kits herein described can be used in connection with pharmaceutical, medical, and veterinary applications, as well as fundamental scientific research and methodologies, as would be identifiable by a skilled person upon reading of the present disclosure.

BRIEF DESCRIPTION OF THE DRAWINGS

The file of this patent contains at least one drawing executed in color. Copies of this patent with color drawings(s) will be provided by the Patent and Trademark Office upon request and payment of the necessary fee.

For a fuller understanding of the nature of the present invention, reference should be had to the following detailed description taken in connection with the accompanying figures.

FIG. 2 shows one embodiment of the $(AT)_n$ sequence with the Dab-labeled deoxythymidine (dT) at the 8th position from the 5'-terminus of the $(AT)_n$ and the Fl-labeled dT at the 34th position from the 5'-terminus of the $(AT)_n$ sequence.

FIG. 3A shows a polyacrylamide gel of FL905 without staining.

FIG. 3B shows fluorescence DNA melting of FL905.

FIG. 3C shows the double-stranded oligomer FL_AT42 carrying a 42 bp AT sequence and two Nt.BbvCI recognition sites (indicated by the arrows) inserted between SphI and BamHI sites of pUC18.

FIG. 14A shows an agarose gel of pAB1 before (lane 2) and after (lane 3) digestion with Nt.BbvCI.

FIG. 14B shows the annealed FL_905 before (lane 3) and after (lane 2) the ligation reaction with T4 DNA ligase.

FIG. 14C shows the DNA supercoiling assay to convert relaxed (rx) pAB1_FL905 (lane 1) into supercoiled (sc) pAB_FL905 (lane 2). Lane 3 is undigested pAB1_FL905 and lane 4 lambda DNA Hind III digest.

FIGS. 14D-14E show the DNA samples after the relaxed pAB-FL905 was purified before (14D) and after (14E) ethidium bromide staining. Lane 2 is sc pAB1_FL905, lanes 3 and 5 are rx pAB1 FL905 and lanes 4 and 6 are nicked pAB1_FL905.

FIG. 15A shows the fluorescence spectra of sc (red line), rx (black line), and nicked (blue line) pAB1_FL905.

FIG. 15B shows the kinetics of the nicking reaction by Nt.BbvCI.

FIG. 15C shows the kinetics of the relaxation reaction by E. coli DNA topoisomerase I.

FIG. 15D shows the kinetics of the supercoiling reaction by E. coli DNA gyrase.

FIG. 17A-17B show the sequence of oligomer FL924 that represents positions 22 to 63 of SEQ ID NO:8. FIG. 17A shows the fluorescence intensity of rx and sc pAB1_FL924 that contains oligomer FL924. FIG. 17B shows the fluorescence spectra of sc (red lines) and rx (black lines) pAB1_FL924.

BRIEF DESCRIPTION OF THE SEQUENCES

Figure 1A:
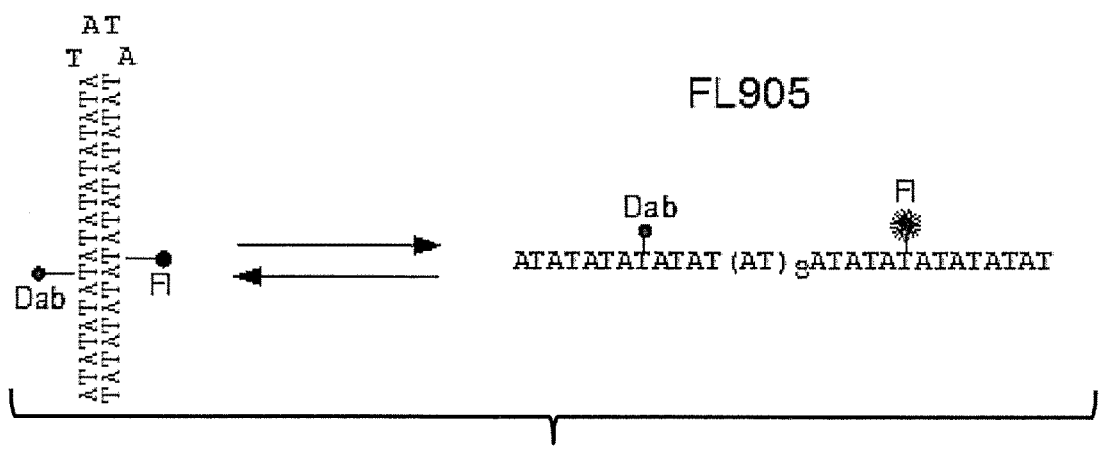
FIG. 1A shows a $(AT)_n$ DNA of FL905 carrying fluorescein (Fl) and dabcyl (Dab) labels and being able to convert from a hairpin structure to an open structure. The sequence shown represents positions 22 to 63 of SEQ ID NO:4.

SEQ ID NO:1 shows a first strand of the double-stranded oligomer FL-AT42.
SEQ ID NO:2 shows the second strand of the double-stranded oligomer FL-AT42 including the 5' and 3' ends cut with SphI and BamHI.
SEQ ID NO:3 shows the synthetic oligonucleotide FL882.
SEQ ID NO:4 shows the synthetic oligonucleotide FL883.
SEQ ID NO:5 shows the synthetic oligonucleotide FL905.
SEQ ID NO:6 shows the synthetic oligonucleotide FL919.
SEQ ID NO:7 shows the synthetic oligonucleotide FL920.
SEQ ID NO:8 shows the synthetic oligonucleotide FL924.

DETAILED DESCRIPTION OF THE INVENTION

The subject invention provides fluorophore-quencher nucleic acid molecules comprising relaxed or supercoiled DNA molecules, their production, optionally, in milligram amounts, and their use to study DNA topology, DNA topoisomerases, DNA gyrases, DNA nicking endonucleases, DNA endonucleases and RNAses.

Because only a few nanograms of any of the fluorophore-quencher nucleic acid comprising circular DNA plasmids are needed for 384-well or 1536-well plates for detection, these DNA plasmids can be used in rapid and efficient high-throughput screening assays to identify inhibitors from the millions of compounds found in small molecule libraries that potentially target DNA topoisomerases, DNA gyrases, DNA nicking endonucleases, DNA endonucleases and RNAses.

In accordance with the subject invention, nucleic acids comprising an adenosine-thymidine repeat $(AT)_n$ sequence comprising at least one fluorophore and at least one quencher conjugated to a deoxythymidine (dT) of the same strand when present in a circular double-stranded DNA molecule can be used for fast detection of changes in DNA topology. It has also been found that a fluorophore and a quencher conjugated to dTs at a specific distance on the same DNA strand of a double-stranded $(AT)_n$ sequence quickly interconvert between an extruded and an unextruded conformation upon supercoiling of the circular DNA. In the supercoiled state, the $(AT)_n$ sequence adopts, for example, a hairpin structure that brings the fluorophore and the quencher into close proximity and leads to the quenching of fluorophore fluorescence. In the relaxed circular DNA molecule, where the $(AT)_n$ is in a double-stranded conformation, the fluorophore and quencher are located at a sufficient distance such that no quenching occurs and the fluorophore fluoresces.

The instant fluorophore-quencher nucleic acid sequences can comprise alternating adenosine-thymidine $(AT)_n$ repeats, or alternatively G-quadruplexes.

In accordance with the subject invention, large amounts of circular plasmids containing the at least one fluorophore and at least one quencher-comprising nucleic acid can be produced, which large amounts make the use of the instant nucleic acids in high throughput screening methods feasible.

The instant fluorophore-quencher comprising $(AT)_n$ nucleic acid sequences have advantageous properties. For example, interconversion between the extruded and unextruded conformation of the fluorophore-quencher nucleic acid sequences occurs with fast kinetics allowing rapid detection of changes in fluorescence as the circular DNA undergoes structural changes upon supercoiling and relaxation. The instant fluorophore-quencher $(AT)_n$ nucleic acids can be used to gauge superhelicity of DNA molecules and detect the presence of DNA topology-affecting enzymes. The instant fluorophore-quencher nucleic acids are well-suited for high-throughput analyses of topology changes of DNA because of the speed of change in DNA conformation and the fast kinetics of changes in fluorescence combined with the ease of mass-production of the instant nucleic acid molecules.

Without wanting to be bound by theory, it is believed that the speed of fluorescence change produced by the instant fluorophore-quencher nucleic acids can be explained by two mechanisms: fast extrusion of a supercoiling-dependent hairpin leading to effective quenching of fluorescence due to optimized proximity of fluorophore and quencher in the hairpin conformation combined with effective removal of quenching due to optimized distance between fluorophore and quencher in the relaxed double-stranded DNA molecule.

In preferred embodiments, the size of the $(AT)_n$ sequence and the distance between the fluorophore and quencher located on the same strand combine fast interconversion between extruded and unextruded conformation, which is promoted by shorter hairpin supporting $(AT)_n$ sequences, with sufficient distance between fluorophore and quencher in the double-stranded state to allow unquenching, which is supported by longer $(AT)_n$ sequences.

The instant fluorophore-quencher nucleic acids combine several features to provide an advantageous system for easy detection and screening for DNA topology-affecting enzymes: at least one fluorophore and at least one quencher at a distance that is chosen to combine direct adjacency of fluorophore and quencher in the stem of the extruded hairpin structure for maximal quenching, sufficient distance in the relaxed double-stranded state for maximal unquenching, and ease of mass-production due to the novel production method disclosed herein.

The circular double-stranded plasmids comprising the instant fluorophore-quencher nucleic acids can be made in small batches or in large milligram amounts. For both small and large batch preparation, a double-stranded oligomer comprising an $(AT)_n$ sequence and two nicking endonuclease recognition sites at each end is provided, wherein the nicking endonuclease recognition sites can be oriented in the same direction, can be oriented in opposite directions, can be recognition sites for the same nicking endonuclease, or can be recognition sites for different nicking endonuclease; such oligomer is ligated to a pre-cut double-stranded DNA plasmid using standard cloning techniques, such that the nicking endonuclease recognition sites are preserved in the double-stranded DNA plasmid and flank the $(AT)_n$ oligomer sequence.

It is contemplated that the $(AT)_n$ sequence between the nicking endonuclease recognition sites of said plasmid undergoes structural changes including formation of hairpin structures and/or cruciform structures upon supercoiling-dependent structural changes of the double-stranded DNA plasmid.

In specific embodiments, a fluorophore-quencher nucleic acid sequence is introduced into the same strand of the $(AT)_n$ sequence of the double-stranded circular plasmid by digesting the plasmid with a nicking enzyme that removes one DNA strand located between the two nicking endonuclease recognition sites. In some embodiments, a nucleic acid containing at least one fluorophore and at least one quencher conjugated to dTs at a predetermined distance is ligated to the nicked sites of the plasmid using standard cloning techniques.

In other embodiments, a fluorophore-comprising nucleic acid sequence is introduced into one strand and a quencher-comprising nucleic acid sequence is introduced into the opposite strand of the $(AT)_n$ sequence of the double-stranded circular plasmid, where the $(AT)_n$ sequence of the double-stranded circular plasmid comprises two nicking sites for a first nicking endonuclease on one strand and two nicking sites for a second nicking endonuclease on the opposite strand. Following nicking of the first strand by a first nicking endonuclease, a fluorophore-conjugated nucleic acid sequence can be ligated between the nicked ends. Subsequently, the opposite strand can be nicked by a second nicking endonuclease and a quencher-conjugated nucleic acid sequence can be ligated between the second nicked ends such that the fluorophore-comprising nucleic acid and the quencher-comprising nucleic acids are located on opposing strands.

For small batch preparation of the fluorophore-quencher comprising circular double-stranded DNA plasmids, the plasmids can be purified by agarose gel electrophoresis or Cesium chloride-ethidium bromide equilibrium gradient banding; however, yields using these methods are limited because isolation of plasmid DNA from agarose gel pieces and extraction of DNA from Cesium chloride-ethidium bromide bands generally result in loss of DNA and, thus, these methods are not suitable for the preparation of large quantities of circular plasmid DNA.

In one embodiment, the method disclosed herein combines the cloning strategy described above employing the described nicking technique and a simple DNA recovery procedure, both of which enable a yield of, for example, 50%, 60%, 70% or up to 80% or more, and, thus, enable the generation of milligram amounts of the fluorophore-quencher nucleic acid comprising circular double-stranded plasmid DNA.

For the large scale production of relaxed fluorophore-quencher comprising circular double-stranded DNA, milligram amounts of a circular double-stranded plasmid DNA comprising an $(AT)_n$ sequence are digested with a nicking endonuclease and phosphorylated oligomer comprising the instant fluorophore-quencher nucleic acid are added and incubated in appropriate conditions to allow annealing of the instant fluorophore-quencher nucleic acid to the single strand of plasmid DNA located between the nicked sites. DNA ligase is added to ligate the fluorophore-quencher nucleic acid to the nicked ends. It has surprisingly been discovered that the yield of double stranded DNA containing the instant fluorophore-quencher nucleic acid can be significantly increased when DNA polymerase and dNTPs are added to the ligation reaction. It has also been determined that the yield can be further increased when the reaction mixture after the ligation reaction is incubated with T5 exonuclease to digest single-stranded oligomer and nicked or gapped double-stranded starting material plasmid DNA. Advantageously, the T5 exonuclease does not digest double-stranded DNA successfully ligated to the instant fluorophore-quencher nucleic acid. The yield of production of fluorophore-quencher comprising circular double-stranded DNA can further be increased by extracting the DNA with phenol twice, precipitating with isopropanol, washing with 70% ethanol, dissolving the DNA pellet and dialyzing the resultant DNA to obtain essentially pure and ready for use relaxed fluorophore-quencher comprising circular double-stranded DNA.

For large scale production of supercoiled fluorophore-quencher comprising circular double-stranded DNA, milligram amounts of a circular double-stranded plasmid DNA comprising an $(AT)_n$ sequence are digested with a nicking endonuclease and phosphorylated oligomers comprising the instant fluorophore-quencher nucleic acid are added and incubated in appropriate conditions to allow annealing of the instant fluorophore-quencher nucleic acid to the single strand of plasmid DNA located between the nicked sites. DNA ligase in the presence of ethidium bromide is added to ligate the fluorophore-quencher nucleic acid to the nicked ends and the procedure as described above, including addition of T5 exonuclease to remove single-stranded oligomers and nicked or gapped double-stranded starting material plasmid DNA, is performed.

Advantageously, the high yield of up to, for example, 80% obtained using the method of the subject invention allows the use of the instant plasmid DNAs to screen small-compound libraries containing millions of compounds using high throughput screening.

In specific embodiments, the double-stranded DNA plasmids comprising at least one fluorophore and at least one quencher on the same strand display maximal fluorescence in the relaxed state because the quencher and fluorophore located on the same strand are separated and no quenching occurs. In contrast, in the supercoiled state of the circular double-stranded plasmid, the fluorophore-quencher comprising $(AT)_n$ nucleic acid strand interconverts from the unextruded to an extruded conformation and due to the close proximity of fluorophore and quencher in the extruded conformation, fluorescence is quenched.

In other embodiments, the double-stranded DNA plasmids comprise at least one fluorophore on one strand and at least one quencher on the opposite strand and display no fluorescence in the relaxed double-stranded state because the fluorophore and quencher on opposite strands are in close proximity such that the fluorescence of the fluorophore is quenched. In contrast, in the supercoiled state of said circular double-stranded plasmids, when the fluorophore-comprising and the quencher-comprising nucleic strands both interconvert from the unextruded to an extruded conformation and form a cruciform structure, the fluorophore and quencher are in such distance as to prevent the quenching of fluorophore fluorescence.

It is contemplated that in some embodiments, the instant circular double-stranded plasmid comprising fluorophore-quencher nucleic acids contain more than one fluorophore-quencher pair, whereas each fluorophore-quencher pair is located in an $(AT)_n$ nucleic acid sequence and forms a hairpin structure upon supercoiling of the circular DNA molecule. In other embodiments, the circular DNA molecule can comprise more than one fluorophore and more than one quencher located within the same $(AT)_n$ nucleic acid sequence, wherein the supercoiling of the circular DNA molecule induces a hairpin comprising more than one fluorophore and more than one quencher with each fluorophore being in close proximity to a quencher in the hairpin conformation to quench fluorophore fluorescence and each fluorophore and each quencher being at a sufficient distance in the relaxed double-stranded conformation to prevent quenching.

In specific embodiments, the $(AT)_n$ sequence of the instant fluorophore-quencher nucleic acid can comprise a low of about 12 AT dinucleotides to a high of about 50 AT dinucleotides. For example, the instant fluorophore-quencher nucleic acid can comprise AT dinucleotide sequences from about 12 ATs to about 17 ATs; about 18 ATs to about 25 ATs; about 26 ATs to about 33 ATs; about 34 to about 41 ATs; or about 42 to about 50 ATs.

In preferred embodiments, the fluorophore-quencher nucleic acid comprises about 20 to about 25 AT dinucleotides. In a more preferred embodiment, the fluorophore-quencher nucleic acid comprises about 20 to about 22 AT dinucleotides. In most preferred embodiments, the fluorophore-quencher nucleic acid comprises 21 AT dinucleotides.

The $(AT)_n$ sequence of the instant nucleic acid can comprise the at least one fluorophore and the at least one quencher conjugated to a deoxythymidine (dT) at a predetermined distance from the 5' end of the $(AT)_n$ sequence. For example, the fluorophore can be conjugated to a dT located at a low distance of fourth position from the 5' start of the $(AT)_n$ sequence to a high distance of about fourteenth position from the 5' start of the $(AT)_n$ sequence. In specific embodiments, the fluorophore can be located at about the fourth; the fifth; the sixth; the seventh; the eighth; the ninth; the tenth; the eleventh; the twelfth; the thirteenth; or the fourteenth position from the start of the $(AT)_n$ sequence.

In some embodiments, the at least one quencher of the fluorophore-quencher nucleic acids can be conjugated to a dT located at a low distance of fourth position from the 5' start of the $(AT)_n$ sequence to a high distance of about fourteenth position. For example, a quencher can be localized at about the fourth; the fifth; the sixth; the seventh; the eighth; the ninth; the tenth; the eleventh; the twelfth; the thirteenth; or the fourteenth position from the start of the $(AT)_n$ sequence of the fluorophore-quencher nucleic acid.

The fluorophore-quencher nucleic acid having a quencher at a location of about fourth to about fourteenth position from the 5' start of the $(AT)_n$ sequence can have a fluorophore located at a low distance of about 28th position from the 5' start of the $(AT)_n$ sequence to a high distance of about the 40th position from the 5' start. For example, a fluorophore-quencher nucleic acid sequence can have a quencher at about the fourth to the fourteenth position from the 5' start of the $(AT)_n$ sequence and a fluorophore at about the 28th; 29th; 30th; the 31st; the 32nd; the 33rd; the 34th; the 35h; the 36th; the 37th; the 38th; the 39th; or the 40th position from the 5' start of the $(AT)_n$ sequence.

The fluorophore-quencher nucleic acid having a fluorophore at a location of about fourth to about fourteenth position from the 5' start of the $(AT)_n$ sequence can have a quencher located at a low distance of about 28th position from the 5' start of the $(AT)_n$ sequence to a high distance of about the 40th position. For example, a fluorophore-quencher nucleic acid sequence can have a quencher at about the fourth to the fourteenth position from the 5' start of the $(AT)_n$ sequence and a fluorophore at about the 28th; 29th; 30th; the 31st; the 32nd; the 33rd; the 34th; the 35th; the 36th; the 37th; the 38th; the 39th; or the 40th position from the 5' start of the $(AT)_n$ sequence.

It is contemplated that the location of the fluorophore and quencher-conjugated dT on the same strand within the $(AT)_n$ sequence is such that the proximity of fluorophore and quencher in an extruded conformation provide maximal quenching and the fluorophore and quencher in an unextruded, double-stranded conformation provide maximal fluorescence of the fluorophore. For optimized detection of fluorescence changes that allows utilization of the instant nucleic acids in high-throughput analyses, it is desirable that the fluorescence in the quenched conformation is as low as possible and the fluorescence in the unquenched conformation is as high as possible combined with the most rapid interconversion from one conformation to the other.

In one embodiment, a distance between the fluorophore and quencher within the $(AT)_n$ sequence of about 25 nucleotides in the instant fluorophore-quencher nucleic acid provides excellent FRET efficiency. It has also been determined that an increase in the distance between fluorophore and quencher to about 29 nucleotides leads to a significant reduction in FRET efficiency, whereas a reduction of the distance to about 21 nucleotides leads to a less significant reduction.

In preferred embodiments, a fluorophore of the nucleic acid is located at about the 6th to about the 10th position from the 5' start of an $(AT)_n$ sequence comprising about 20 to 22 AT dinucleotides, $(AT)_{20-22}$, and a quencher is located at about the 32nd to the 36th position from the 5' start of the $(AT)_{20-22}$ sequence. In a more preferred embodiment, a fluorophore of the nucleic acid is located at about the 8th to about the 10th position from the 5' start of an $(AT)_n$ sequence comprising about 20 to 22 AT dinucleotides, $(AT)_{20-22}$, and a quencher is located at about the 34th to the 36th position from the 5' start of the $(AT)_{20-22}$ sequence.

In a most preferred embodiment, a fluorophore is located at the 8th position from the 5' start of an AT sequence comprising 21 AT, $(AT)_{21}$, and a quencher is located at the 34th position from the 5' start of the $(AT)_{21}$ sequence, whereby the fluorophore-conjugated dT and the quencher-conjugated dT are separated by 25 nucleotides.

Many fluorophores can be used to make the instant fluorophore-quencher nucleic acids. For example, the fluorophore can be 6-FAM (fluoroscein), Cy3™, TAMRA™, JOE, Cy5™, Cy5.5™, MAX, TET™, Carboxy-X-Rhodamine, TYE™ 563, TYE™ 665, TYE 705, Yakima Yellow®, Hexachlorofluorescein, TEX 615, Alexa Fluor® 488, Alexa Fluor® 532, Alexa Fluor® 546, Alexa Fluor® 594, Alexa Fluor® 647, Alexa Fluor® 660, Alexa Fluor® 750m 5' IRDye® 700, 5'IRDye® 800, 5' IRDye®800CW, ATTO™ 488, ATTO™ 532, ATTO™ 550, ATTO™ 565, ATTO™ Rho101, ATTO™ 590, ATTO™ 633, ATTO™ 647, Rhodamine Green™-X, Rhodamine Red™-X, 5-TAMRA™, WEllRED D2, WellRED D3, WellRED D4, Texas Red®-X, Lightcycler® 640, DY 750, BODIPY FL, EDANS, or IAEDANS.

The quenchers used to make the instant fluorophore-quencher nucleic acids can be, for example, Dabcyl, DDQ-I, Eclipse, Iowa Black FQ, BHQ-1, QSY-7, BHQ-2, DDQ-II, Iowa Black RQ, QSY-21, or BHQ-3.

Preferred fluorophore-quencher pairs useful in the instant fluorophore-quencher nucleic acids are shown in Tables 1 to 3 below.

TABLE 1

Fluorophore and quencher selection

| Fluorophore | Max absorbance (nm) | Max emission (nm) | Quencher |
|---|---|---|---|
| 6-FAM (Fluorescein) | 494 | 521 | Dabcyl/BHQ-1 |
| TET | 521 | 536 | Dabcyl/BHQ-1 |
| HEX | 535 | 556 | Dabcyl/BHQ-1 |
| Cy3 | 552 | 570 | BHQ-2 |
| TAMRA | 565 | 580 | BHQ-2 |
| Alexa Fluor 568 | 578 | 603 | BHQ-2 |
| Texas Red-X | 583 | 603 | BHQ-2 |
| Cy 5 | 646 | 667 | BHQ-3 |
| Alexa Fluor 680 | 679 | 702 | BHQ-3 |
| Cy5.5 | 683 | 707 | BHQ-3 |
| Cy 7 | 743 | 767 | BHQ-3 |

TABLE 2

Quencher spatial data

| Quencher | Max absorbance (nm) | Quenching range (nm) |
|---|---|---|
| Dabcyl | 453 | 380-530 |
| BHQ-1 | 534 | 480-580 |
| BHQ-2 | 579 | 560-650 |
| BHQ-3 | 650 | 620-730 |

TABLE 3

Common donor-acceptor pairs for FRET with Foster Radius (R0)

| Donor | Acceptor | R0 (Å) |
|---|---|---|
| Fluorescein | Tetramethylrhodamine | 55 |
| IAEDANS | Fluorescein | 46 |
| EDANS | Dabcyl | 33 |
| Fluorescein | Fluorescein | 44 |
| BODIPY FL | BODIPY FL | 57 |
| Fluorescein | QSY 7 | 61 |

The circular double-stranded DNA molecules comprising the instant fluorophore-quencher sequences can be used to detect and quantify the presence of DNA topology affecting enzymes in a biological sample.

In a specific embodiment, the circular double-stranded DNA comprising at least one fluorophore and at least one quencher on the same strand undergoes supercoiling in the presence of a DNA gyrase, wherein the fluorophore-quencher comprising nucleic acid sequence undergoes rapid localized DNA conformation transition, i.e. interconversion from the unextruded conformation in the double-stranded DNA to an extruded conformation in the supercoiled state and quenching of fluorophore fluorescence occurs based on the close proximity of the fluorophore and quencher in the extruded conformation. In the presence of a DNA topoisomerase, on the contrary, supercoiled circular DNA molecules comprising the instant fluorophore-quencher nucleic acid on the same strand undergo relaxation, wherein the fluorophore-quencher comprising nucleic acid sequence undergoes localized DNA conformation transition from the extruded conformation of the supercoiled state to the unextruded conformation of the relaxed, double-stranded state and fluorescence occurs because the fluorophore and quencher are located in a sufficient distance that prevents quenching.

Therefore, the instant fluorophore-quencher nucleic acid sequence present on the same stand of a circular DNA molecule can be used to detect DNA topology-affecting enzymes, including DNA topoisomerases, DNA gyrases, DNA nicking endonucleases, and DNA endonucleases, in a highly efficient manner.

When the fluorophore-comprising nucleic acid sequence and the quencher-comprising nucleic acid sequence are present on opposite strands of a circular DNA molecule, the presence of DNA gyrase can be detected when relaxed circular plasmid DNA is supercoiled and the fluorophore and quencher positioned on opposite strands are located on the ends or tips of cruciform structures formed in the extruded conformation such that quenching cannot occur. The presence of DNA topoisomerase, in contrast, can be detected when supercoiled circular plasmid DNA is relaxed and the fluorophore and quencher positioned on opposite strands are in close proximity such that the fluorescence of the fluorophore is quenched.

In specific embodiments, the fluorophore of the nucleic acid is fluorescein and the quencher is dabcyl. In more specific embodiments, the distance between fluorescein and the dabcyl-conjugated dT in the $(AT)_n$ sequence can be as low as about 14 nucleotides to as high as about 32 nucleotides. In preferred embodiments, the distance between the fluorescein and the dabcyl-conjugated dT is from about 14 to about 16 nucleotides; from about 17 to about 20 nucleotides; from about 21 to about 23 nucleotides; from 24 to about 26 nucleotides; and from about 27 to about 32 nucleotides. In more preferred embodiments, the distance between fluorescein and dabcyl-conjugated dT is from about 21 to about 25 nucleotides. In most preferred embodiments, the distance between fluorescein and dabcyl-conjugated dT is 25 nucleotides.

In one embodiment, the fluorescein fluorophore and the dabcyl quencher having a distance of about 88 Å to about 100 Å in the double-stranded, relaxed conformation of the instant nucleic acid, i.e., being conjugated to dTs with about 25 nucleotides between the fluorescein-conjugated dT and the dabcyl-conjugated dT, results in high fluorescence of fluorescein. In contrast, when the fluorescein fluorophore and the dabcyl quencher are in the extruded hairpin conformation the distance between fluorescein and dabcyl is about 20 Å and the fluorescence of fluorescein is efficiently quenched by dabcyl. Advantageously, the FRET efficiency of the instant fluorescein-dabcyl comprising nucleic acid having about 25 nucleotides between the fluorescein-conjugated dT and the dabcyl-conjugated dT is about 0.83.

In some embodiments, the fluorophore is TAMRA and the quencher is BHQ2 and the distance between the TAMRA- and the BHQ2-conjugated dT in the $(AT)_n$ sequence is 25 nucleotides.

It has been discovered that a fluorescein-dabcyl comprising nucleic acid having a reduced distance between fluorescein and dabcyl of about 21 nucleotides can result in a FRET efficiency of about 0.75, whereas an increase in the distance between fluorescein and dabcyl to about 29 nucleotides can result in a FRET efficiency of only 0.51. It has further been discovered that the use of different fluorophore-quencher pairs, such as TAMRA and BHQ2, at the same optimized distance of 25 nucleotides results in a FRET efficiency of 0.8 similar to the FRET efficiency of the fluorescein-dabcyl comprising nucleic acid, albeit with a lower fluorescence of the TAMRA fluorophore compared to fluorescein.

The FRET efficiency of the fluorophore and quencher of the instant nucleic acids can range from about 0.45 to about 0.90. For example, the FRET efficiency can be from about 0.45 to about 0.5; from about 0.51 to about 0.59; from about 0.6 to about 0.69; from about 0.7 to about 0.79; from about 0.8 to about 0.82; from about 0.83 to about 0.85; from about 0.86 to about 0.88 and from about 0.89 to about 0.9.

It has been discovered that a supercoiled fluorescein-dabcyl comprising plasmid, pAB1_FL905, can be interconverted to a relaxed state by exposure to DNA topoisomerase with the fluorescein and dabcyl-dTs having maximal distance in the relaxed state and resulting in removal of quenching with a half-maximal increase in fluorescence in about 25 seconds.

It was further discovered that exposure of a supercoiled fluorescein-dabcyl-comprising plasmid, pAB1_FL905, to DNA nicking endonuclease can result in rapid nicking with a half-maximal increase in fluorescence of the nicked plasmid in about 15 seconds.

In further embodiments, the circular plasmid comprising a fluorophore-quencher nucleic acid can have nicking endonuclease recognition sites outside the fluorophore-quencher nucleic acid sequence, which second nicking endonuclease recognition sites differ from the nicking endonuclease recognition sites of the fluorophore-quencher sequence. The second nicking endonuclease recognition sites can be in the same orientation and can be recognition sites for the same nicking endonuclease or for different endonucleases. In specific embodiments, the circular DNA plasmid comprising nicking endonuclease recognition sites outside the fluorophore-quencher containing nucleic acid sequence can be used to detect the presence of nicking endonucleases in a sample, where in the presence of a nicking endonuclease the circular DNA plasmid is relaxed and a change in fluorescence occurs.

In other embodiments, the circular DNA plasmid comprising nicking endonuclease recognition sites outside the fluorophore-quencher nucleic acid sequence can be nicked with a nicking endonuclease and a RNA oligomer can be inserted between the nicked ends. The RNA oligomer-comprising plasmid can be used to detect RNAse activity in a sample. For example, a supercoiled DNA plasmid comprising a RNA oligomer can be relaxed by exposure to an RNAse and the change in fluorescence in the relaxed state plasmid is indicative of the presence of the RNAse.

In another embodiment, the fluorophore-quencher nucleic acid comprising double-stranded plasmid can be used to detect DNA endonuclease activity in a sample. For example, the circular DNA plasmid comprising a fluorophore-quencher containing nucleic acid sequence can be used in the supercoiled state and exposed to a DNAse endonuclease, which endonuclease cleaves the double-stranded DNA at specific endonuclease recognition sites and the linearized plasmid DNA having the fluorophore and quencher on the same strand and separated in the linearized state fluoresces, which fluorescence is indicative of the presence of the DNA endonuclease.

Advantageously, the instant circular DNA plasmids comprising fluorophore-quencher containing nucleic acid sequences can be used to detect the presence of, and study the properties of, for example, DNA topoisomerases, DNA gyrases, DNA nicking endonucleases, DNA endonucleases, and RNAses and the presence of inhibitors of DNA topoisomerases, DNA gyrases, DNA nicking endonucleases, DNA endonucleases, and RNAses.

The instant circular DNA plasmids comprising fluorophore-quencher nucleic acid sequences can also be used to screen for inhibitors of DNA topoisomerase, DNA endonuclease, and DNA nicking endonuclease activity. In one method, a sample suspected of containing an inhibitor of a DNA topoisomerase, DNA endonuclease, or DNA nicking endonuclease is added to a DNA topoisomerase, DNA endonuclease, or DNA nicking endonuclease and a supercoiled DNA plasmid comprising a fluorophore-quencher nucleic acid sequence one the same strand and an increase in fluorescence in the sample is indicative of the presence of uninhibited DNA topoisomerase, DNA endonuclease, or DNA nicking endonuclease activity, whereas the absence of fluorescence is indicative of the presence of an inhibitor of the DNA topoisomerase, DNA endonuclease, or DNA nicking endonuclease, respectively.

A suitable method for screening for inhibitors of RNAse activity in a sample can use a supercoiled plasmid comprising a fluorophore-quencher nucleic acid sequence on the same strand and a RNA oligomer, exposing said plasmid to an RNAse and a sample suspected of containing an inhibitor of a RNAse and detect an increase in fluorescence in the sample when no inhibitor is present, i.e., the DNA is relaxed by the RNAse, and detect the absence of fluorescence in a sample where an inhibitor is present, i.e., the supercoiled DNA is not relaxed because the inhibitor inhibits the relaxing activity of the RNAse.

Also provided are kits for screening inhibitors of DNA topoisomerases, DNA gyrases, DNA endonucleases, DNA nicking endonucleases or RNAses. The kit can comprise, for example, a circular double-stranded DNA plasmid comprising the fluorophore-quencher nucleic acid on the same strand, a DNA topoisomerase, DNA endonuclease, DNA nicking endonuclease or RNAses, wherein the plasmid is in the supercoiled conformation and the kit is used to detect inhibitors of the DNA topoisomerase, DNA endonuclease, DNA nicking endonuclease or RNAse. The kit can further comprise a circular double-stranded DNA plasmid comprising the fluorophore-quencher nucleic acid, and a DNA gyrase, wherein the plasmid is in the relaxed conformation and the kit is used to detect inhibitors of the DNA gyrase.

The kits may further be used in the methods described herein. The kits may also include at least one reagent and/or instructions for their use. Also, the kits may include one or more containers filled with reagent(s) and/or one or more molecules of the invention. The kits may also comprise a control composition. In certain embodiments, the kits may additionally include reagents and means for detecting the labels provided on the molecules of the invention. The means of allowing detection may be by conjugation of detectable labels or substrates, such as fluorescent compounds, enzymes, radioisotopes, heavy atoms, reporter genes, luminescent compounds, etc. As it would be understood by those skilled in the art, additional detection or labeling methodologies may be used in the kits provided. Further, any pair of fluorophores (donor fluorophore and acceptor fluorophore) that undergoes FRET can be used in the kits.

Among the DNA topoisomerases that can be detected using the instant fluorophore-quencher nucleic acid comprising circular plasmid DNAs are topoisomerases including type I; type IA; type IB; type IIA; type IV; bacterial topoisomerases, including E. coli topoisomerase I, bacterial topoisomerase IV, bacterial DNA gyrase; and human topoisomerases I and IIa and other topoisomerase IA and IB topoisomerases, and other topoisomerase IIA and IIB topoisomerases. The methods can also be used to screen for yeast topoisomerase II, mammalian topoisomerase IIa and IIb, prokakryotic DNA topoisomerase III, yeast DNA topoisomerase III, mammalian DNA topoisomerase IIIa and IIIb, and poxvirus and vaccinia DNA topoisomerases.

Among the RNAses that can be detected using the RNA oligomer-comprising fluorophore-quencher comprising circular plasmid DNAs are RNAse H and other RNAses.

Among the DNA nicking endonucleases useful in the generation of the instant fluorophore-quencher nucleic acid comprising circular plasmids and/or which nicking endonucleases can be detected using the instant fluorophore-quencher nucleic acid comprising circular plasmid DNAs are Nt.BspQI, Nt.CviPII, Nt.BstNBI, Nb.BtsI, Nb.BsrDI, Nt.AlwI, Nb.BbvCI, Nt.BbvCI, Nb.BsmI, Nt.BsmAI, Nb.Bpu10I and nonspecific nicking endonucleases, such as mung bean nuclease.

Among the DNA endonucleases that can be detected using the instant fluorophore-quencher nucleic acid comprising circular plasmid DNAs are any commercially available DNA endonucleases that cut double-stranded plasmid DNA and for which the double-stranded plasmid DNA contains an endonuclease recognition site.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

Following are examples that illustrate procedures for practicing the invention. These examples should not be construed as limiting.

EXAMPLES

Example 1—Materials and Methods

Restriction enzymes Nt.BbvCI, SphI, BamHI, E. coli DNA gyrase, and T4 DNA ligase were purchased from New England Biolabs (Beverly, Mass., USA). E. coli DNA topoisomerase I was purified as described previously[19]. The following synthetic oligonucleotides were purchased from MWG-Biotech, Inc. (Huntsville, Ala.): FL882 (5'-CCC TCAGCCCGACAGCACGAGACGA-TATATATATATATATATATATATATATATAT ATATATATGGGCCAACCAACCAGCCCCTCAGCG-3') (SEQ ID NO:3), FL883 (5'-GATCCGCTGAGGGGCTG-GTTGGTTGGCCCATATATATATATATATATATATATAT ATATATATATATATCGTCTCGTGCTGTCGGGCT-GAGGGCATG-3') (SEQ ID NO:4), FL905 (5'-TCAGC-CCGACAGCACGAGACGATATATA[Dab-dT] ATATATATA TATATATATATATA[FL-dT] ATATATATGGGCCAACCAACCAGCCCC-3') (SEQ ID NO:5), FL919 (5'-TCAGCCCGACAGCACGAGACGA-TATA[Dab-dT]ATATATATATAT ATATATATATATATA [Fl-dT]ATATATGGGCCAACCAACCAGCCCC-3') (SEQ ID NO:6), FL920 (5'-TCAGCCCGACAGCACGAGAC-GATATATATA[Dab-dT]ATATATAT ATATATATATATA[Fl-dt]ATATATATATGGGCCAACCAACCAGCCCC-3') (SEQ ID NO:7), and FL924 (5'-TCAGCCCGACAGCACGA-GACGATATATA[BHQ2-dT]ATATAT ATATATATATATATATATA [TAM-dT]ATATATATGGGC-CAACCAACCAGCCCC-3') (SEQ ID NO:8) where DabdT, Fl-dT, BHQ2-dT, and TAM-dT represent dabcyl-dT, fluorescein-dT, BHQ2-dT, and TAMRA-dT, respectively. QIAquick Nucleotide Removal Kit and QIAquick Gel Extraction Kit were obtained from Qiagen, Inc (Valencia, Calif.).

Plasmids

Plasmid pAB1 (2,757 bp) was constructed by inserting a 95 bp synthetic DNA fragment FL_AT42 (the annealing product of FL882 and FL883) between the SphI and BamHI sites of pUC18. DNA sequencing was used to verify the inserted DNA sequence.

Fluorescence Spectroscopy

Fluorescence measurements can be performed using an ISS, Inc., PC1 photo counting spectrofluorimeter with an excitation wavelength of 470 nm and bandwidth resolution of ±4 nm or a Biotek Synergy H1 Hybrid Plate Reader with an excitation wavelength of 482 nm.

Molecular Modeling

DNA molecular models can be generated using HyperChem 8.0.

Example 2—Strategy to Construct Relaxed (Rx) and Supercoiled (SC) PAB1_FL905

Alternating adenine-thymine sequences [$(AT)_n$] undergo very rapid cruciform formation, as no detectable kinetic barrier prevents rapid interconversion between extruded and unextruded conformations in supercoiled (sc) plasmid DNA templates (5). This property of [(AT)] was utilized to monitor supercoiling changes of plasmid DNA templates.

Figure 1B:
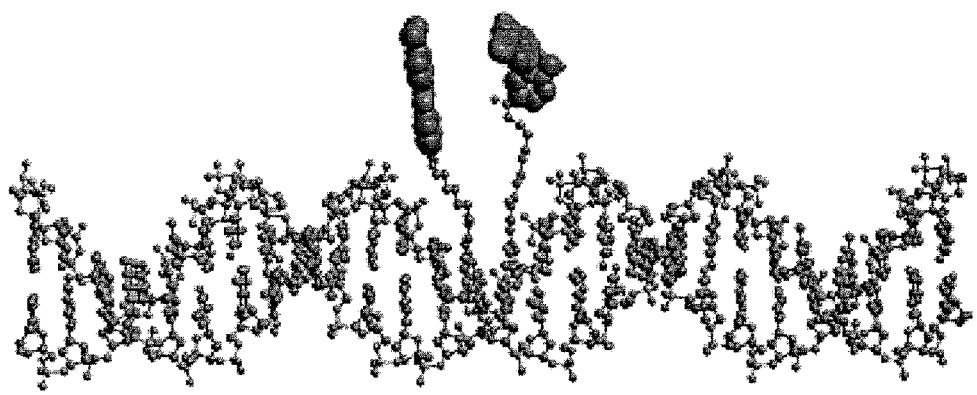
FIG. 1B shows a model of the FL905 DNA with the Fl and Dab labels in proximity to each other when the $(AT)_n$ of FL905 adopts the hairpin structure.
Figure 1C:
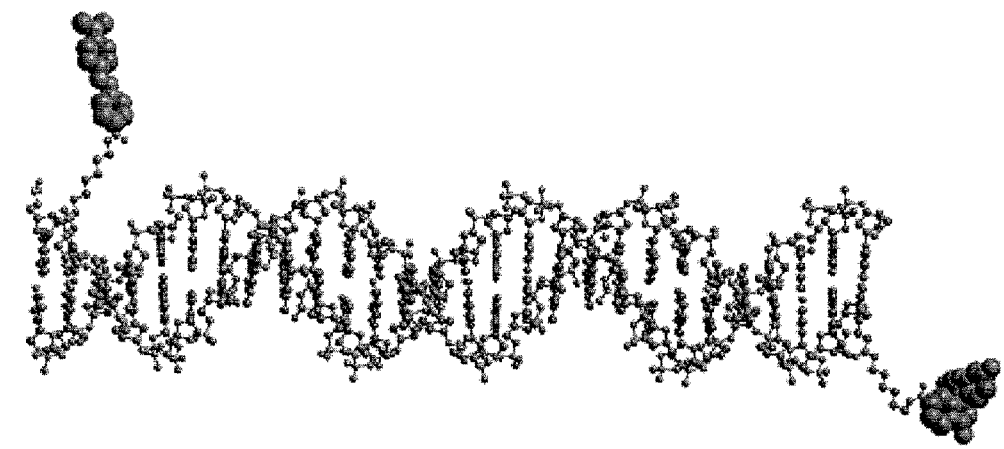
FIG. 1C shows a model of the FL905 DNA with the Fl and Dab labels being away from each other when the $(AT)_n$ sequence is in the double stranded state.

A 82 nucleotide (nt) DNA oligomer, FL905, was designed that contains a dabcyl (Dab)-labeled deoxythymidine (dT) at 29th position from the 5'-end (the $8^{th}$ position of the AT sequence from the 5'end) and a fluorescein (Fl)-labeled dT at 55th position from the 5'-end (the $34^{th}$ position of the AT sequence from the 5'end (FIG. 1A and FIG. 2). FIG. 3A shows that FL905 has intrinsic fluorescence before EB staining. If the 42 nt AT sequence adopts the hairpin structure, both the fluorescein and dabcyl are in close proximity in the major groove (~20 Å; FIG. 1B). The fluorescence of fluorescein in this conformation is greatly quenched. In contrast, when the 42 nt AT sequence adopts the double-stranded DNA form, the distance between the fluorescein and dabcyl is more than 88.4 Å for B-form DNA (26 bp×3.4 Å=88.4 Å) and can be 100 Å (FIG. 1C). The fluorescence of fluorescein in the double-stranded DNA is not quenched. With increasing temperature, a four-fold fluorescence intensity change of fluorescein can be observed as the 42 nt AT hairpin structure is melted (FIG. 3B). Thus, fluorescence resonance energy transfer (FRET) can be used to study the interconversion between extruded and unextruded conformations of FL905.

Figure 3D:
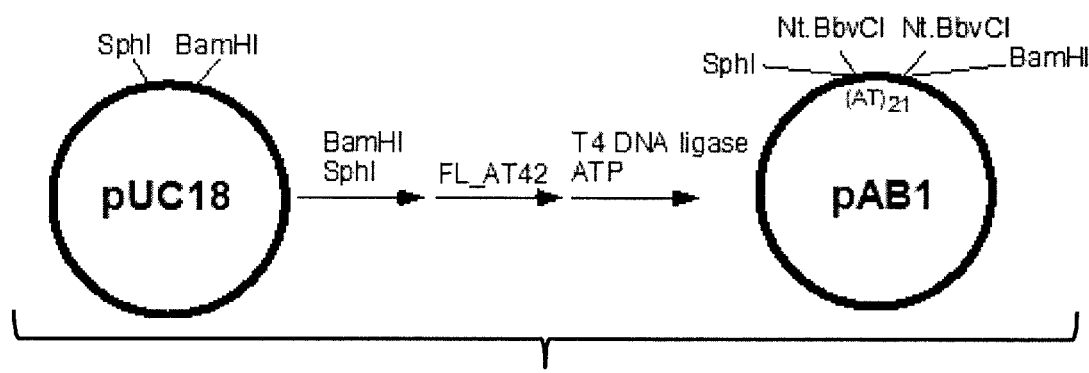
FIG. 3D shows the cloning steps to insert FL_AT42 into SpHI and BamHI sites to yield pAB1 that contains two Nt.BbvCI sites and the 42 bp AT sequence located between the two Nt.BbvCI sites.
Figure 4A:
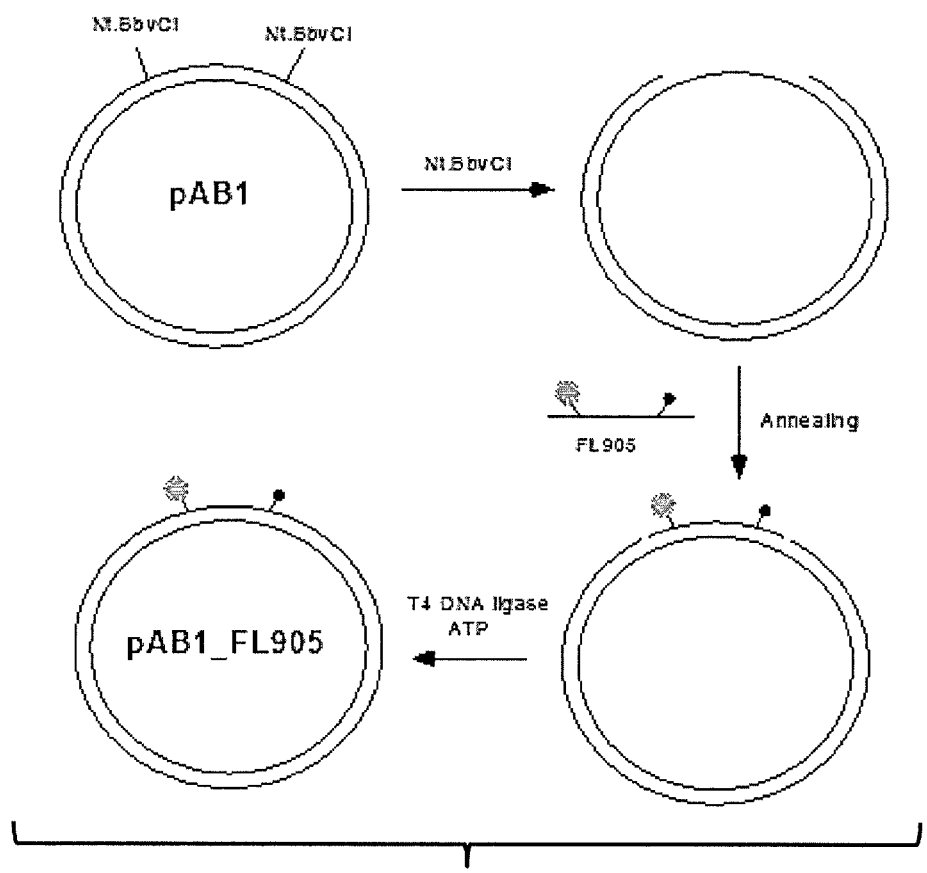
FIG. 4A shows the strategy employed to insert FL905 DNA into the $(AT)_{42}$ nucleic acid sequence of pAB1.
Figure 4B:
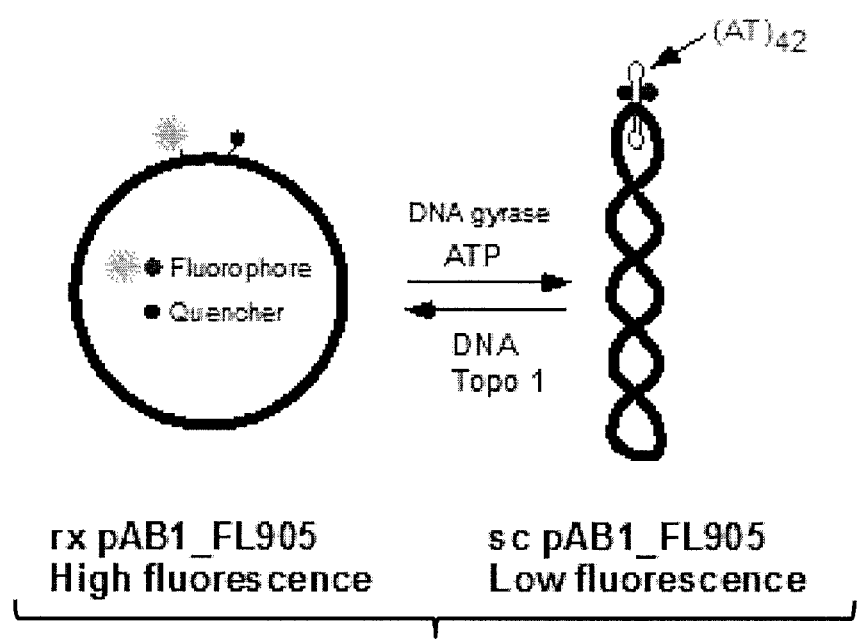
FIG. 4B shows the generation of supercoiled (sc) pAB1_FL905 from relaxed (rx) pAB1_FL905 using E. coli DNA gyrase and the relaxation of sc pAB1_FL905 using DNA topoisomerase 1.
Figure 6:
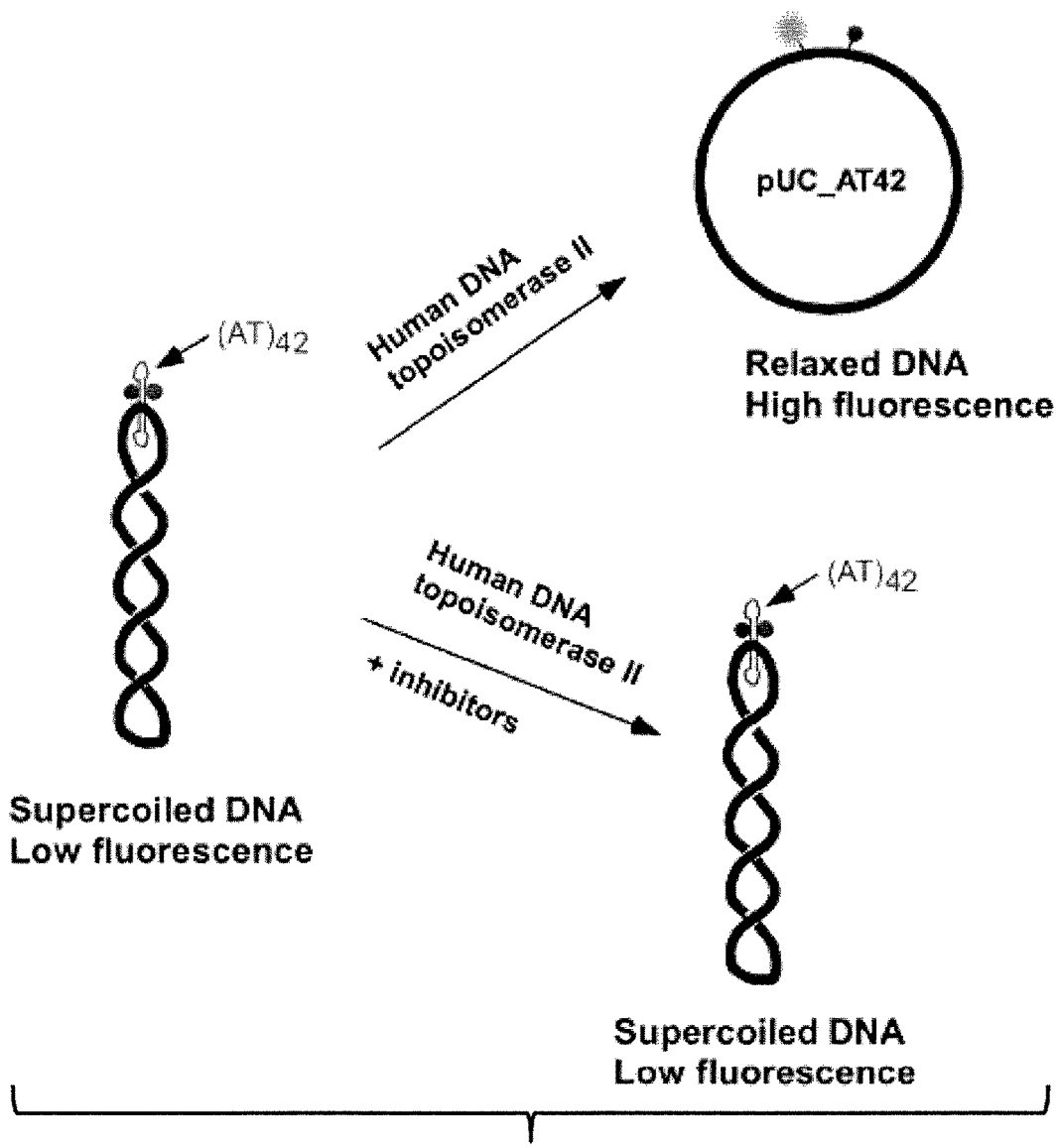
FIG. 6 shows strategies to study and screen inhibitors targeting DNA topoisomerases that relax supercoiled DNA molecules. The Inhibition $IC_{50}$ may be determined by a titration experiment.
Figure 7:
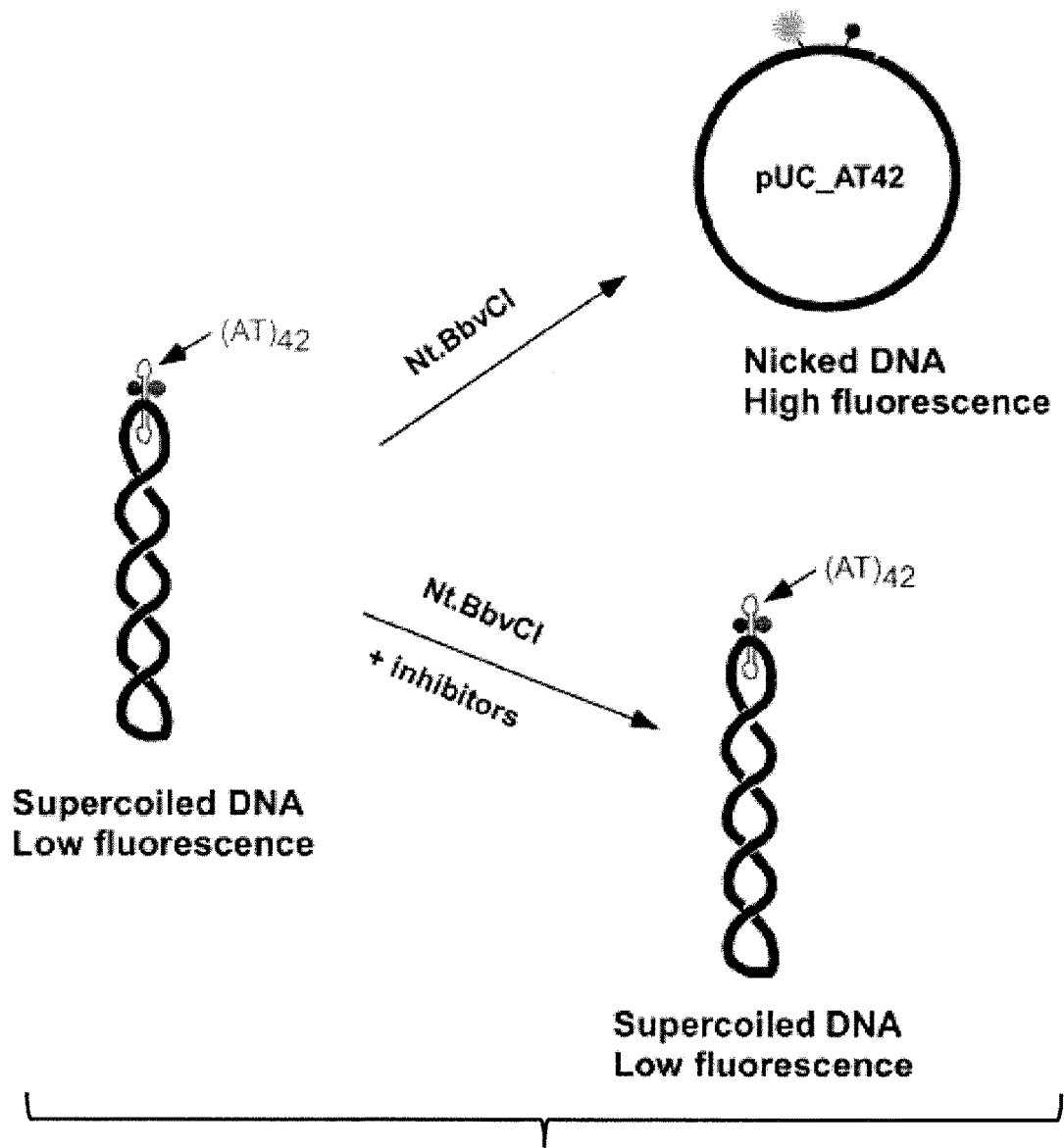
FIG. 7 shows strategies to study and screen inhibitors targeting DNA nicking enzymes.
Figure 8:
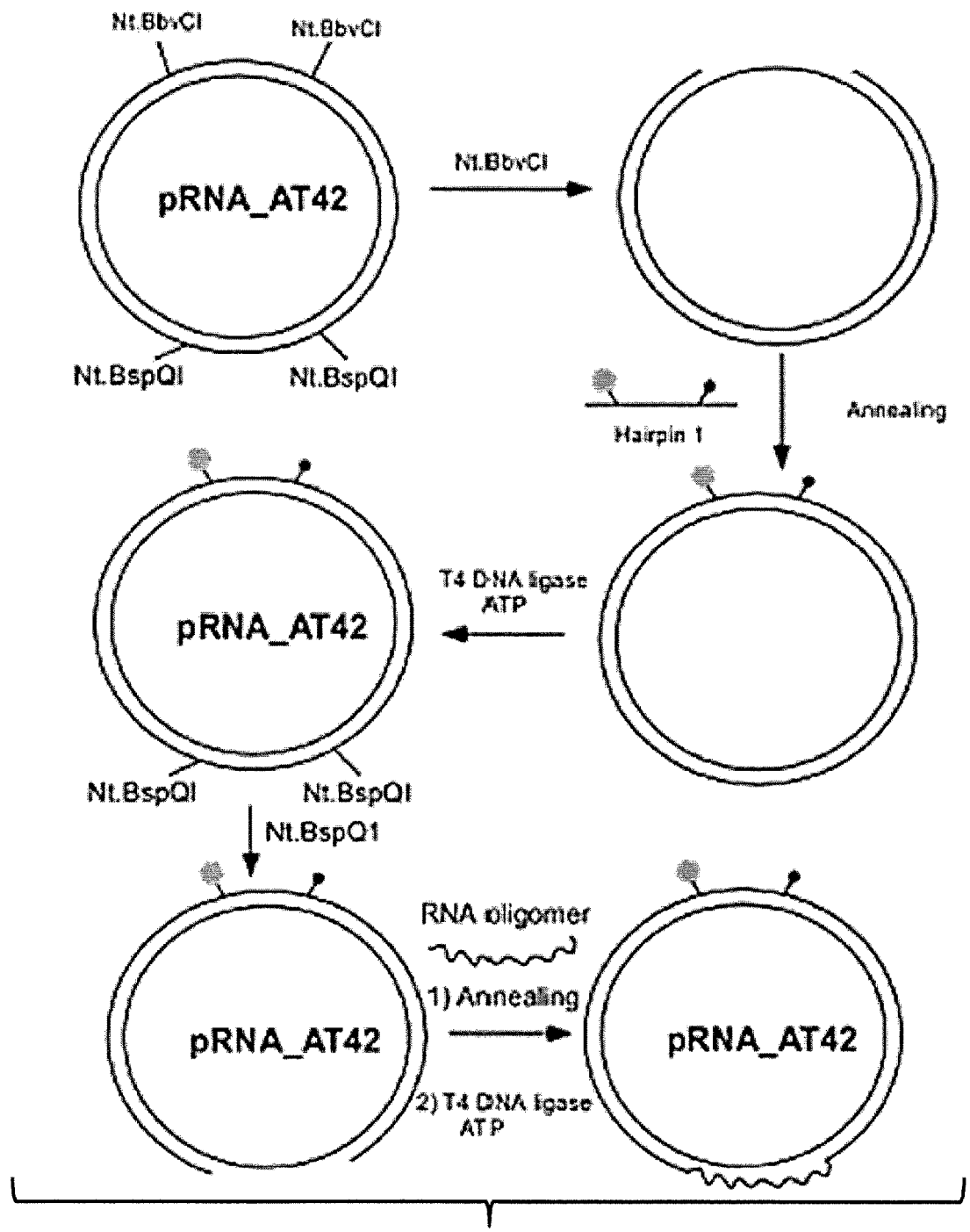
FIG. 8 shows a strategy to construct fluorescently labeled circular plasmid DNA molecules that contain a RNA oligomer inserted between two Nt.BspQI sites.
Figure 9:
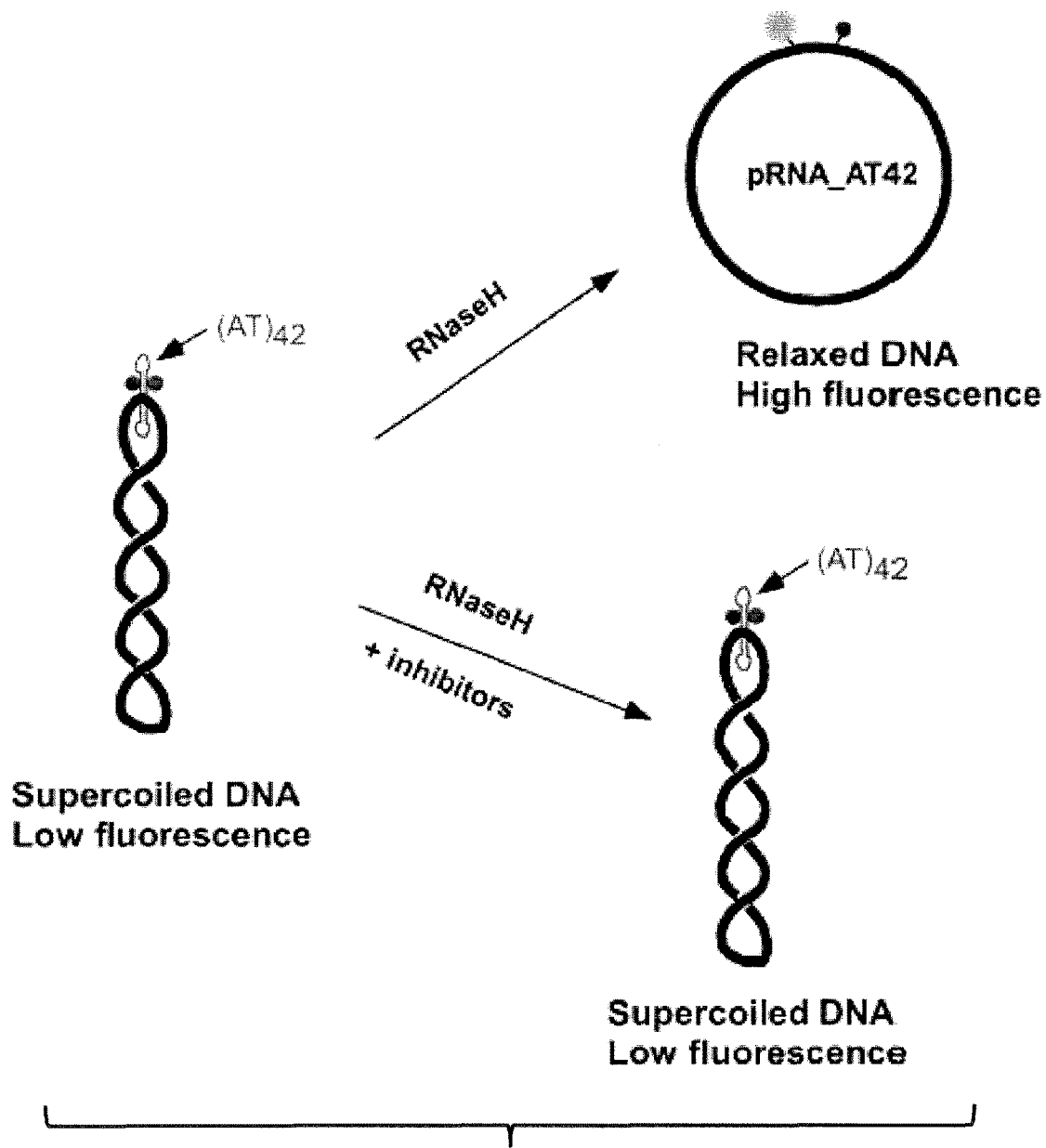
FIG. 9 shows supercoiled fluorescence-labeled DNA molecules with an RNA oligomer that can be used to study RNase H or other RNases and to screen inhibitors targeting these RNases, whereby supercoiling of the DNA molecule containing a RNA oligomer is induced with DNA gyrase, relaxation of the supercoiled DNA is induced with RNAse H, and relaxation is inhibited in the presence of RNAseH inhibitors.
Figure 10:
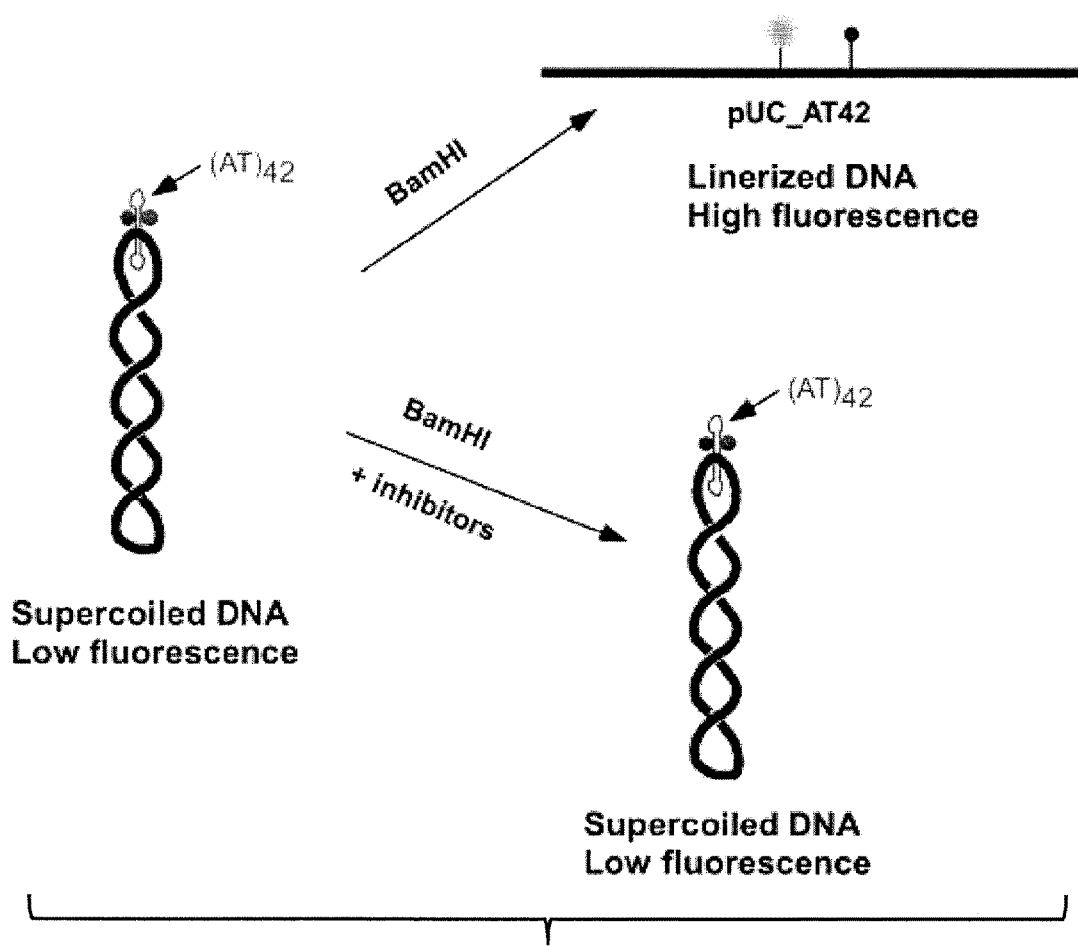
FIG. 10 shows strategies to study and screen inhibitors targeting double-stranded DNA endonucleases.

A circular plasmid, pAB1, can be constructed by inserting a synthetic double-stranded oligomer, FL_AT42 that carries the 42 bp AT sequence (FIG. 3C), between the SphI and BamHI sites of pUC18 (FIG. 3D). The circular plasmid pAB1 can also contain two nicking edonuclease Nt.BbvCI recongnition sites in the same orientation. In this way, DNA oligomer FL905 can be inserted between the two Nt.BbvCI sites according to generate the relaxed pAB1_FL905 (FIG. 4A). Supercoiled (sc) pAB1_FL905 can be generated through the treatment of rx pAB1_FL905 with bacterial DNA gyrase in the presence of ATP (FIG. 4B). Rx and sc pAB1_FL905 are powerful tools to study DNA topology and topoisomerases by FRET and inhibitors of DNA gyrases (Figures SA), inhibitors of DNA topoisomerases (FIG. 6), inhibitors of DNA nicking endonnucelases (FIG. 7), inhibitors of RNAses (FIG. 9), inhibitors of DNA endonucleases (FIG. 10).

Figure 11:
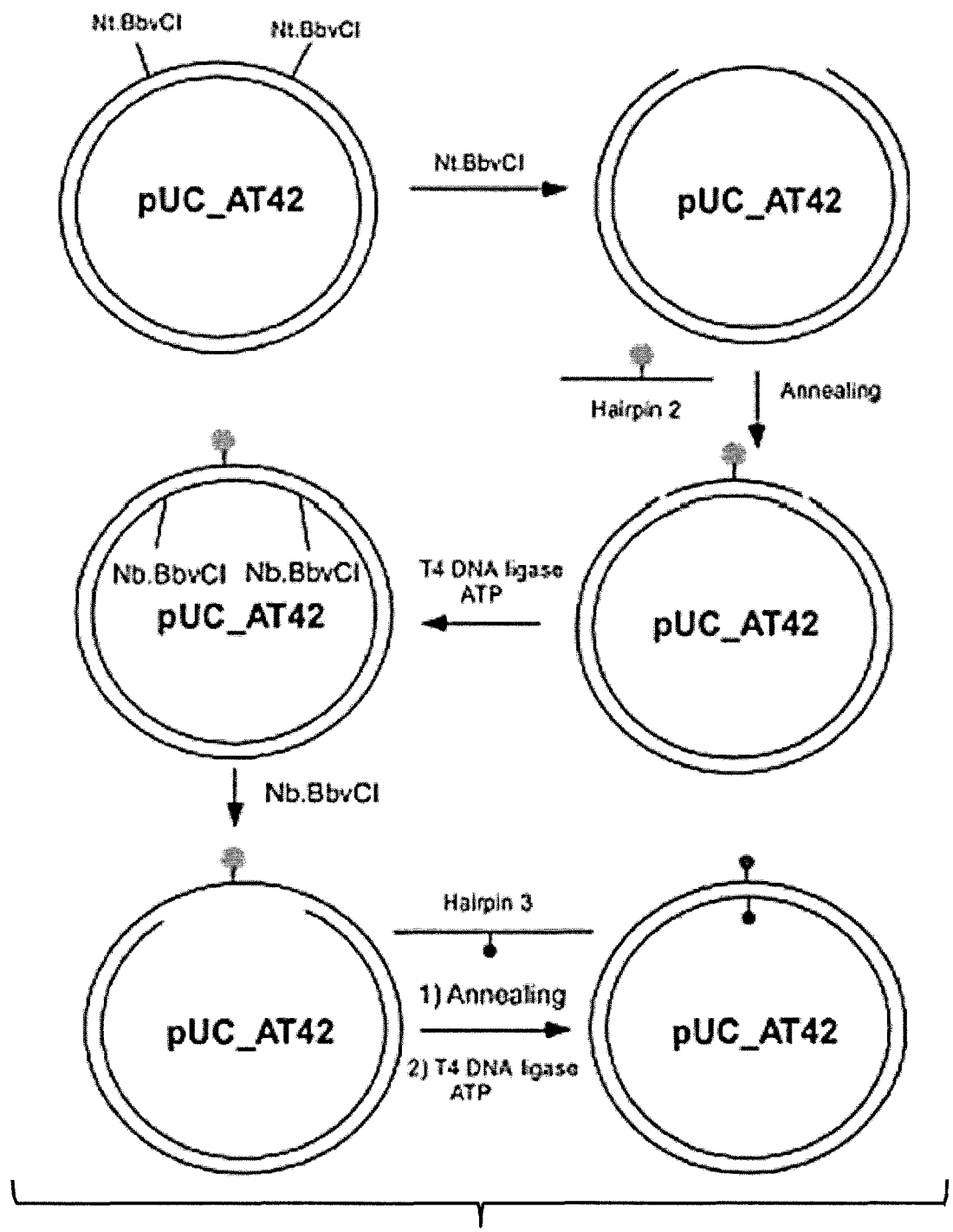
FIG. 11 shows a strategy to construct fluorescently labeled circular DNA molecules with the fluorescein (FL)-labeled deoxythymidine (dT) on one strand and the Dabcyl (Dab)-labeled dT on the opposite strand.
Figure 12:
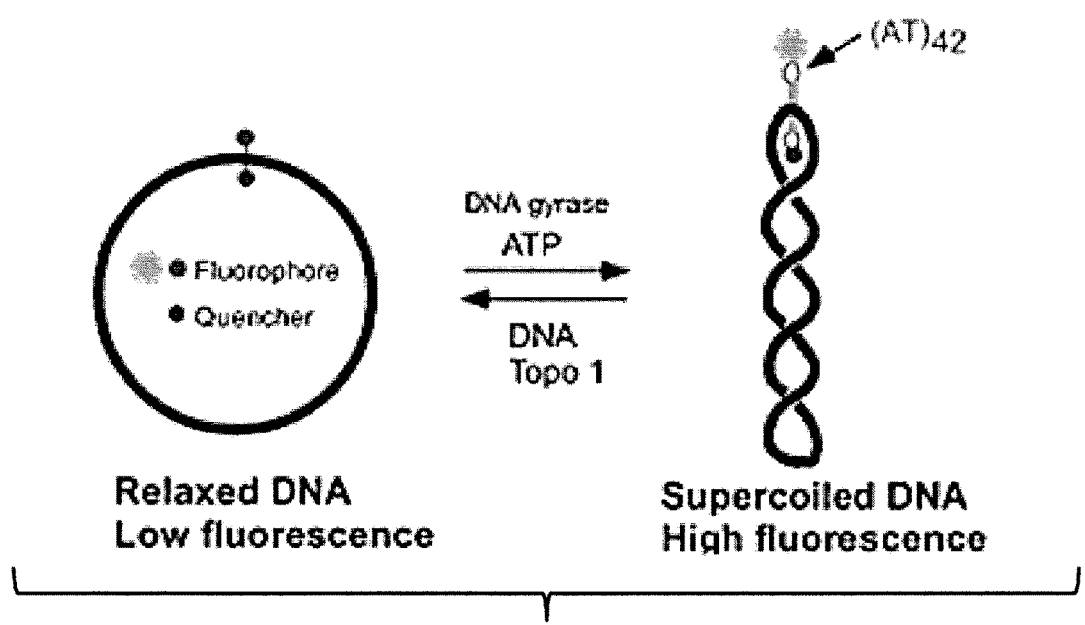
FIG. 12 illustrates that the DNA sequences inserted between the Nt.BbvCI and Nb.BbvCI sites on opposite strands contain supercoiling-sensitive structures such as hairpins and formation of the hairpins leads to high fluorescence because of the distance between the fluorophore and the quencher on the hairpins of opposite DNA strands.

The circular plasmid pAB1 can also contain two nicking endonuclease Nt.BbvCI recongnition sites on one strand and two nicking endonuclease Nb.BbvCI recognition sites on the opposite strand. In this way, a DNA oligomer carrying a fluorophore can be inserted between the two Nt.BbvCI sites and a DNA oligomer carrying a quencher can be inserted between the two Nb.BbvCI sites (FIG. 11). Supercoiling of such plasmid results in high fluorescence and relaxation in low fluorescence (FIG. 12).

Figure 13:
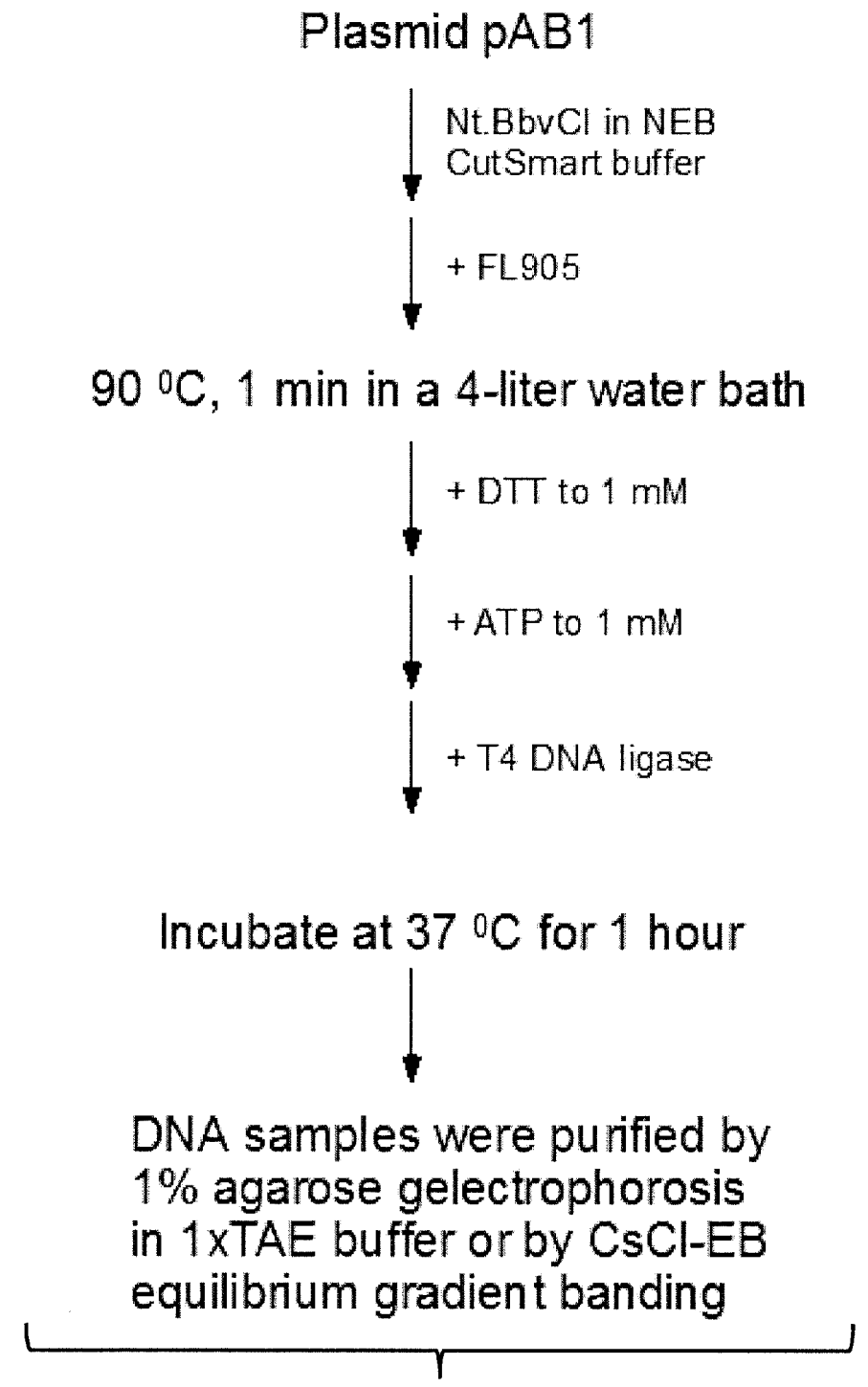
FIG. 13 shows the strategy to produce relaxed (rx) pAB1_FL905.

Example 3—Small and Large Scale Production of Relaxed and Supercoiled Plasmids (FIG. 13)

For the synthesis of relaxed (rx) and supercoiled (sc) pAB1_FL905, pAB1_FL919, pAB1_FL920, and pAB1_FL924 on a small scale of reaction, 10 μg of pAB1 (~5.7 μmol) can be digested by 25 units of Nt.BbvCI in 200 μL of 1× CutSmart Buffer (50 mM Potassium Acetate, 20 mM Tris-Acetate, 10 mM Magnesium Acetate, 100 μg/mL BSA, pH 7.9). After the digestion, 80 pmol of phosphorylated FL905 can be added into the reaction mixture; the reaction mixture can be incubated at 90° C. in a 4-liter water bath for one minute and then cooled down to room temperature in the water bath (~4 to 5 hours or overnight). To generate rx pAB1_FL905, 300 units of T4 DNA ligase can be added into the reaction mixtures in the presence of 10 mM of DTT and 2 mM of ATP (final concentrations). The reaction mixtures can be incubated at 37° C. to seal the nicks and yield rx pAB1_FL905. The rx pAB1_FL905 can be separated by 1% agarose gel electrophoresis and purified by QIAquick Gel Extraction Kit. Typically, ~6 μg of rx pAB1_FL905 (~60% yield) can be obtained. To produce sc pAB1_FL905, 1 μg of rx pAB1_FL905 can be treated with 5 units of E. coli DNA gyrase for 1 hour at 37° C. The sc pAB1_FL905 can be purified by QIAquick Nucleotide Removal Kit or separated by 1% agarose gel and purified by QIAquick Gel Extraction Kit. An alternative procedure can also be used to produce sc pAB1_FL905. First, the annealed product of the Nt.BbvCI digested pAB1 and FL905 can be purified by QIAquick Nucleotide Removal Kit. The purified DNA sample (~1 μg) can be ligated with 300 units of T4 DNA ligase in the presence of 5 units of DNA gyrase. The sc and rx pAB1_FL905 can be separated by using a 1% agarose gel and purified by using QIAquick Gel Extraction Kit. Rx and sc pAB1_FL919, pAB1_FL920, and pAB1_FL924 can also be generated similarly.

For a typical large scale of reaction, 1 mg of pAB1 (~570 pmol) can be digested by 2500 units of Nt.BbvCI in 20 ml of 1× CutSmart Buffer for one hour at 37° C. After the digestion, 11,400 pmol of phosphorylated FL905 can be added into the reaction mixture. The reaction mixture can be incubated at 90° C. in a 4-liter water bath for two minutes and then cooled down to room temperature in the water bath (~4 to 5 hours or overnight). To generate rx pAB1_FL905, 25,000 units of T4 DNA ligase (NEB) can be added into the reaction mixtures in the presence of 10 mM of DTT and 2 mM of ATP (final concentrations). The reaction mixtures can be incubated at 37° C. to seal the nicks and yield rx pAB1_FL905. To increase the yield of rx pAB1_FL905, 750 units of T4 DNA polymerase and 200 μM of dNTPs can be added to the reaction mixture. Then, 5,000 units of T5 exonuclease (NEB) can be added into the reaction mixture to digest single-stranded (ss) oligomer FL905 and nicked or gapped pAB1 except rx pAB1_FL905 (T5 exonuclease only digested ss FL905 and nicked pAB1 and does not degrade rx or sc pAB1_FL905). The rx pAB1_FL905 sample can be extracted with 20 mL of phenol twice, precipitated with 0.7 volume of isopropanol, washed once with 70% ethanol, dissolved into 0.5 mL of 10 mM Tris-HCl, pH 8.0, and dialyzed against 1,000 mL of 10 mM Tris-HCl, pH 8.0. The rx pAB1_FL905 is essentially pure and ready for use. It was observed that on average ~0.8 mg of rx pAB1_FL905 from 1 mg of pAB1 can be generated (~80% yield).

To generate sc pAB1_FL905, 25,000 units of T4 DNA ligase (NEB) can be added into the reaction mixtures in the presence of 25 µM ethidium bromide, 10 mM of DTT and 2 mM of ATP (final concentrations). The reaction mixtures can be incubated at 37° C. to seal the nicks and yield sc pAB1_FL905. To increase the yield of sc pAB1_FL905, 750 units of T4 DNA polymerase and 200 µM of dNTPs can be added to the reaction mixture. Then, 5,000 units of T5 exonuclease (NEB) can be added into the reaction mixture to digest single-stranded (ss) oligomer FL905 and nicked or gapped pAB1 except sc pAB1_FL905. The sc pAB1_FL905 sample can be extracted with 20 mL of phenol twice, precipitated with 0.7 volume of isopropanol, washed once with 70% ethanol, dissolved into 0.5 mL of 10 mM Tris-HCl, pH 8.0, and dialyzed against 1,000 mL of 10 mM Tris-HCl, pH 8.0. The sc pAB1_FL905 is essentially pure and ready for use. It was observed that on average 0.8 mg of sc pAB1_FL905 from 1 mg of pAB1 can be generated (~80% yield).

Usually it is required to purify rx and sc pAB1-FL905 by agarose gel electrophoresis or CsCl-EB banding, which is very difficult to generate pure rx and sc pAB1_FL905 in the milligram range. The use of T5 exonuclease followed by phenol extraction and isopropanol precipitation significantly simplifies the purification procedure. This procedure makes the production of large amounts of rx and sc pAB1_FL905 feasible. Because of this procedure, it is possible to use rx or sc pAB1_FL905 to high throughput screen small compound libraries containing millions of compounds. Additionally, this new procedure also greatly increases the yield of rx and sc pAB1_FL905.

Example 4—Fluorescence Properties of Relaxed, Nicked, Supercoiled PAB1_FL905

The strategy shown in FIG. 13 can be used to produce large quantities of rx pAB1-FL905. For example ~0.5 mg of rx pAB1_FL905 and ~0.6 mg of sc pAB1_FL905 can be produced and purified by CsCl-EB equilibrium gradient banding with approximately 60% yield. Rx and sc pAB1_FL905 have intrinsic fluorescence before EB staining (FIG. 14D).

Fluorescence measurements can be performed using an ISS, Inc., PC1 photo counting spectrofluorimeter with an excitation wavelength of 470 nm and bandwidth resolution of ±4 nm or a Biotek Synergy H1 Hybrid Plate Reader with an excitation wavelength of 482 nm.

When comparing fluorescence properties of sc, rx, and nicked (nk) pAB1_FL905, the fluorescence intensity of rx or nk pAB1_FL905 is significantly higher than that of the sc pAB1_FL905 (FIG. 15A). The kinetic results of pAB1_FL905 reacting with three different enzymes show that Nt.BbvCI can quickly nick sc pAB1_FL905 with a half-life of 15 seconds (FIG. 15B) continuing that $(AT)_n$ can undergo very rapid hairpin and/or cruciform formation, as no detectable kinetic barrier prevents rapid interconversion between extruded and unextruded conformations in sc plasmid DNA templates. This result demonstrates that pAB1_FL905 is a good DNA substrate to study DNA topology and topoisomerases by FRET.

Large amounts of *E. coli* DNA topoisomerase I can rapidly relax sc pAB1_FL905 (FIG. 15C). The kinetics of *E. coli* DNA gyrase are relatively slow (FIG. 15D).

Example 5—Fluorescence Properties of Relaxed, Nicked, Supercoiled PAB1_FL919 and PAB1_FL920

Figure 16A:
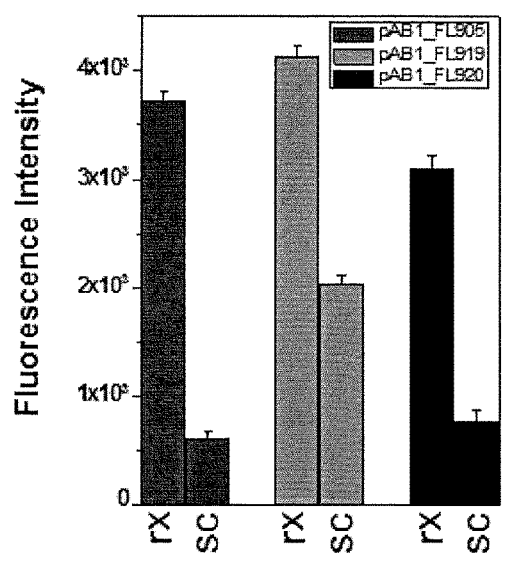
FIG. 16A shows the fluorescence intensity of rx and sc pAB1_FL905, pAB1_FL919, and pAB1_FL920.
Figure 16B:
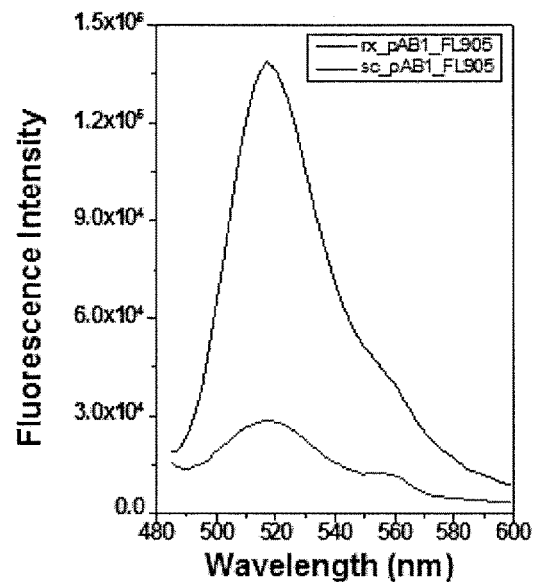
FIG. 16B shows fluorescence spectra of sc (red lines) and rx (black lines) pAB1_FL905.
Figure 16C:
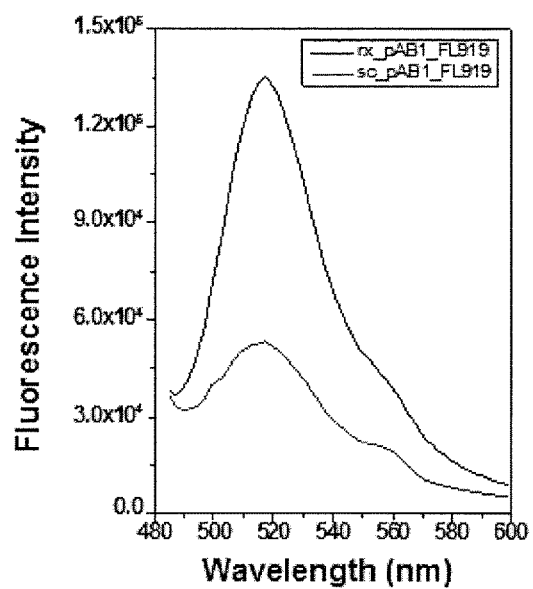
FIG. 16C shows fluorescence spectra of sc (red lines) and rx (black lines) pAB1_FL919.
Figure 16D:
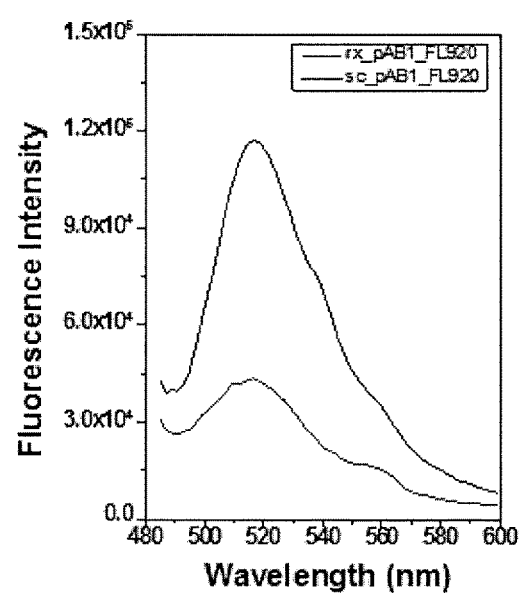
FIG. 16D shows fluorescence spectra of sc (red lines) and rx (black lines) pAB1_FL920.

Similar fluorescence-labeled oligomers, FL919 and FL920, can be generated that contain a dabcyl-labeled dT at 27th and 31$^{st}$ position, and a fluorescein-labeled dT at 57th and 53rd position from the 5'-end, respectively. In these oligomers, the distance between the dabcyl and fluorescein is different for FL905, FL919, and FL920. FL924 carries a BHQ2-labeled dT at 29th position from the 5'-end, i.e. the 8$^{th}$ position of the AT sequence from the 5'end and a TAMRA-labeled dT at 55th position from the 5'-end, i.e. the 34$^{th}$ position of the AT sequence from the 5'end (FIGS. 17A-17B). These three oligomers can be inserted between the two Nt.BbvCI sites of pAB1 to yield rx and sc pAB1_FL919, pAB1_FL920, and pAB1_FL924. Similar to pAB1_FL905, the fluorescence intensity of rx pAB1_FL919, pAB1_FL920, and pAB1_FL924 is significantly higher than that of the sc DNA molecules (FIGS. 16A-16D and FIGS. 17A-17B). However, the FRET efficiency of pAB1_FL919 and pAB1_FL920 is lower than that of pAB1_FL905 (FIG. 16A). Therefore, FL905 has the optimal distance between dabcyl and fluorescein for studying supercoiling-dependent transitions of pAB1 by FRET. The fluorescence intensity of pAB1_FL924 is lower than that of pAB1_FL905 although the FRET efficiency is similar for both DNA molecules.

Example 6—Gyrase Inhibition Assay

Figure 18A:
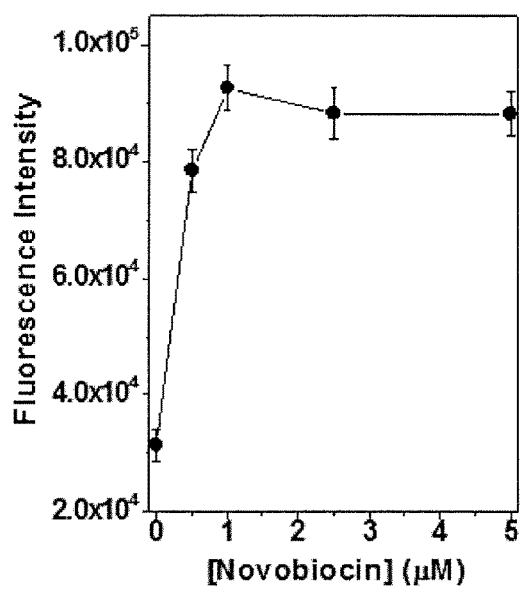
FIG. 18A shows DNA supercoiling reactions of pAB1_FL905 in the presence of novobiocin.
Figure 18B:
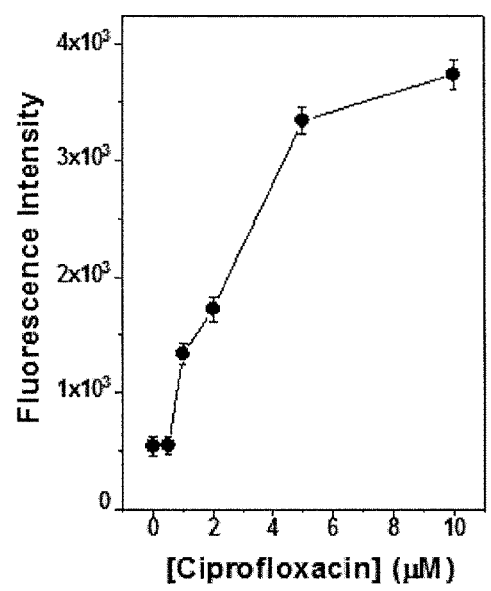
FIG. 18B shows DNA supercoiling reactions of pAB1_FL905 in the presence of ciprofloxacin.

DNA gyrase inhibition assays can be performed in 50 µL of 1× gyrase buffer (35 mM Tris-HCl, 24 mM KCl, 4 mM $MgCl_2$, 2 mM DTT, 1.75 mM ATP, 5 mM spermidine, 0.1 mg/mL BSA, 6.5% glycerol, pH7.5) containing 560 ng of rx pAB1_FL905 and can be equilibrated to 37° C. 20 units of DNA gyrase can be used to supercoil the rx pAB1_FL905 in the presence of different concentrations of novobiocin and ciprofloxacin (FIGS. 18A-18B). The fluorescence intensity at $\lambda_{em}$=521 nm can be monitored with $\lambda_{ex}$=470 nm in a microplate reader. The IC50 values can be estimated by nonlinear fitting of the following equation:

$$F = F_{min} + \frac{F_{max} - F_{min}}{1 + 10^{(log(IC50) - x)P}}$$

where F is the fluorescence intensity at the x concentration of an inhibitor. $F_{max}$ and $F_{min}$ are the maximum and minimum fluorescence of the DNA sample, respectively. P is a slope parameter.

Example 7—Potential Applications

Figure 5A:
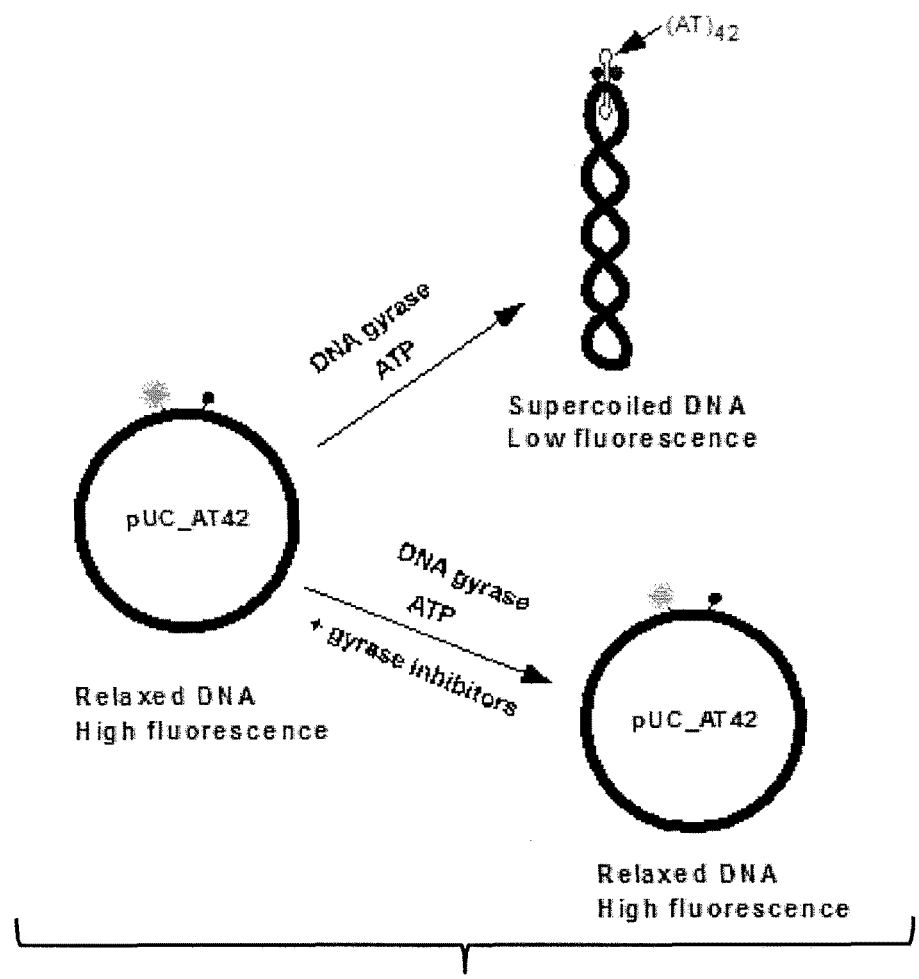
FIGS. 5A-5B show strategies to study DNA gyrase and to screen inhibitors targeting DNA gyrases. The inhibition $IC_{50}$ may be determined by a titration experiment.
Figure 5B:
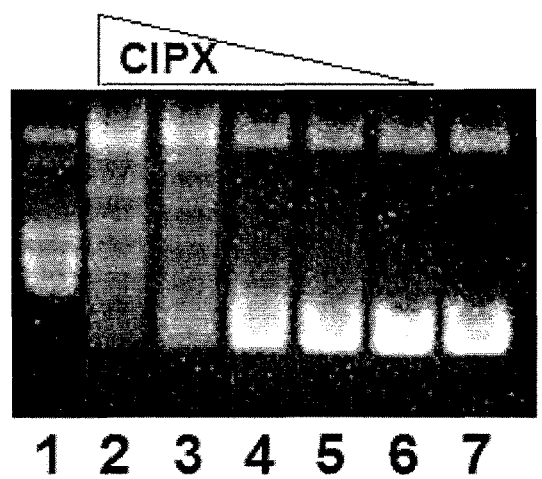

Rx or sc, fluorescently labeled pAB1_FL905 or similar DNA molecules can have many potential applications. They can be used to study supercoiling-dependent DNA topological changes or determine biochemical properties and kinetics of various DNA topoisomerases. In a preferred application, these DNA molecules can be used to screen inhibitors or compounds targeting different DNA topoisomerases since many of these compounds are either anticancer drugs, such as doxorubicin, or antibiotics, such as ciprofloxacin. FIG. 5A shows a strategy for identifying bacterial DNA gyrase inhibitors. In the absence of gyrase inhibitors, bacterial DNA gyrase is capable of converting rx DNA templates into sc DNA molecules (FIG. 5B). As demonstrated above, this conversion results in quenching of fluorescence of pAB1_FL905. However, DNA gyrase inhibitors can inhibit this conversion. In this way, the fluorescence intensity of rx pAB1_FL905 is not changed. A titration experiment can yield an inhibition IC50 for the gyrase inhibitor. According to this strategy, titration experiments can be performed in which different concentrations of novobiocin and ciprofloxacin can be added into DNA supercoiling assays. FIGS. 18A-18B shows the results for novobiocin and ciprofloxacin, both of which can potently inhibit the activities of DNA gyrase with an estimated IC50 of 0.48±0.14 and 2.57±1.62 µM, respectively. Agarose gel electrophoresis can be used to confirm that these antibiotics indeed potently inhibit DNA gyrases activities FIG. 5B. Due to simplicity, this FRET assay can be easily adapted to a high throughput format to identify gyrase inhibitors from millions of compounds found in small molecule libraries. Similar assays can be used to identify inhibitors targeting other DNA topoisomerase, such human DNA topoisomerase I and II.

The instant methods can be used, for example, in antibiotic screening kits to screen for inhibitors that target bacterial DNA gyrase. These DNA gyrase inhibitors can be developed into potent antibiotics. The screening kits can include, for example, the following components: relaxed pAB1_FL905 or a similar product, *E. coli* DNA gyrase, 5×DNA gyrase buffer, ATP, and novobiocin and/or ciprofloxacin as positive control.

Antibiotic screening kits can also be used to screen for inhibitors that target bacterial DNA topoisomerase I. The screening kits can include, for example, the following components: supercoiled pAB1_FL905 or a similar product, *E. coli* DNA topoisomerase I, and 10×DNA topoisomerase I buffer. Screening kits can also be used to screen for anticancer drugs that target human DNA topoisomerase I. The screening kits can include, for example, the following components: supercoiled pAB1_FL905 or a similar product, human DNA topoisomerase I, and 10×DNA topoisomerase I buffer. Finally, screening kits can be used to screen for anticancer drugs that target human DNA topoisomerase II. The screening kits can include, for example, the following components: supercoiled pAB1_FL905 or a similar product, human DNA topoisomerase II, and 10×DNA topoisomerase I buffer.

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Roychoudhury, S., Makin, K. M., Twinem, T. L., Stanton, D. T., Nelson, S. L., & Catrenich, C. E. (2003) Development and use of a high-throughput bacterial DNA gyrase assay to identify mammalian topoisomerase II inhibitors with whole-cell anticancer activity. *J. Biomol. Screen.* 8, 157-163.
2. Maxwell, A., Burton, N. P., & O'Hagan, N. (2006) High-throughput assays for DNA gyrase and other topoisomerases. *Nucleic Acids Res.* 34, e104.
3. Shapiro, A., Jahic, H., Prasad, S., Ehmann, D., Thresher, J., Gao, N., & Hajec, L. (2010) A homogeneous, high-throughput fluorescence anisotropy-based DNA supercoiling assay. *J. Biomol. Screen.* 15, 1088-1098.
4. Jude, K. M., Hartland, A., & Berger, J. M. (2013) Real-time detection of DNA topological changes with a fluorescently labeled cruciform. *Nucleic Acids Res.* 41, e133.
5. Greaves, D. R., Patient, R. K., & Lilley, D. M. (1985) Facile cruciform formation by an (AT) 34 sequence from a *Xenopus* globin gene. *J Mol. Biol.* 185, 461-478.

The invention claimed is:

1. A method of screening for inhibitors targeting DNA topoisomerases, DNA gyrases, DNA endonucleases, or DNA nicking endonucleases, the method comprising:

providing a sample suspected of containing an inhibitor of a DNA topoisomerase, DNA gyrase, DNA endonuclease, or DNA nicking endonuclease;

adding a circular supercoiled double-stranded plasmid comprising a nucleic acid sequence comprising an adenosine-thymidine dinucleotide repeat $(AT)_n$ sequence, characterized in that n is at least 12, the $(AT)_n$ sequence comprises at least one fluorophore and at least one quencher, each conjugated to a deoxythymidine (dT), and the fluorophore-conjugated dT and the quencher-conjugated dT are separated by at least 14 nucleotides and are located on the same DNA strand to the sample suspected of containing an inhibitor of a DNA topoisomerase, DNA endonuclease, or DNA nicking endonuclease; or adding a circular relaxed double-stranded plasmid comprising a nucleic acid sequence comprising an adenosine-thymidine dinucleotide repeat $(AT)_n$ sequence, characterized in that n is at least 12, the $(AT)_n$ sequence comprises at least one fluorophore and at least one quencher, each conjugated to a deoxythymidine (dT), and the fluorophore-conjugated dT and the quencher-conjugated dT are separated by at least 14 nucleotides and are located on the same DNA strand to the sample suspected of containing an inhibitor of a DNA gyrase, adding a DNA topoisomerase, DNA endonuclease, or DNA nicking endonuclease to the sample containing the circular supercoiled double-stranded plasmid; or adding a DNA gyrase to the sample containing the circular relaxed double-stranded plasmid;

quantifying fluorescence in the sample; and quantifying the amount of inhibitor present in the sample based on the fluorescence measured in the sample compared to the fluorescence measured in a control sample containing only the DNA topoisomerase, DNA endonuclease, or DNA nicking endonuclease and the circular supercoiled double-stranded plasmid or containing only the DNA gyrase and the circular relaxed double-stranded plasmid;

characterized in that the fluorescence in the control sample containing the DNA topoisomerase, DNA endonuclease, or DNA nicking endonuclease is high due to the interconversion of the circular supercoiled double-stranded plasmid to a relaxed conformation in the presence of the DNA topoisomerase, DNA endonuclease, or DNA nicking endonuclease; and the fluorescence in the sample is lower than in the control sample if the sample contains an inhibitor of the DNA topoisomerase, DNA endonuclease, or DNA nicking endonuclease; or characterized in that the fluorescence in the control sample containing the DNA gyrase is low due to the interconversion of the circular relaxed double-stranded plasmid to a supercoiled conformation in the presence of the DNA gyrase; and the fluorescence in the sample is higher than in the control sample if the sample contains an inhibitor of the DNA gyrase.

2. The method, according to claim 1, comprising:
adding a circular supercoiled double-stranded plasmid or a circular relaxed double-stranded plasmid both comprising a nucleic acid sequence comprising an $(AT)_n$ sequence, characterized in that n is at least 12, the $(AT)_n$ sequence comprises at least one fluorophore and at least one quencher, each conjugated to a deoxythymidine (dT), and the fluorophore-conjugated dT and the quencher-conjugated dT are separated by at least 14 nucleotides and are located on the opposite DNA strand.

3. The method according to claim 1, comprising:
adding a circular supercoiled double-stranded plasmid or a circular relaxed double-stranded plasmid both comprising a nucleic acid sequence comprising an $(AT)_n$ sequence, characterized in that n is at least 12, the $(AT)_n$ sequence comprises at least one fluorophore and at least one quencher, each conjugated to a deoxythymidine (dT), and the fluorophore-conjugated dT and the quencher-conjugated dT are separated by 25 nucleotides and are located on the same DNA strand.

4. The method, according to claim 1, comprising:
adding a circular supercoiled double-stranded plasmid or a circular relaxed double-stranded plasmid both comprising a nucleic acid sequence comprising an $(AT)_n$ sequence, characterized in that n is at least 12, the $(AT)_n$ sequence comprises at least one fluorophore and at least one quencher, each conjugated to a deoxythymidine (dT), and the fluorophore-conjugated dT and the quencher-conjugated dT are separated by 25 nucleotides and are located on the opposite DNA strand.

5. The method according to claim 1, characterized in that a half-maximal increase in fluorescence in the control sample containing only a DNA topoisomerase occurs within 30 seconds.

6. The method according to claim 1, characterized in that a half-maximal increase in fluorescence in the control sample containing only a DNA nicking endonuclease occurs within 20 seconds.

7. A method of screening for inhibitors targeting RNAses, the method comprising:
providing a sample suspected of containing an inhibitor of a RNAse;
adding a circular supercoiled double-stranded plasmid comprising a nucleic acid sequence comprising an adenosine-thymidine dinucleotide repeat $(AT)_n$ sequence, characterized in that n is at least 12, the $(AT)_n$ sequence comprises at least one fluorophore and at least one quencher, each conjugated to a deoxythymidine (dT), and the fluorophore-conjugated dT and the quencher-conjugated dT are separated by at least 14 nucleotides and are located on the same DNA strand, and further comprising a nucleic acid sequence comprising at least one RNA oligomer located on the same strand as the at least one fluorophore and the at least one quencher;
adding a RNAse;
quantifying fluorescence in the sample; and
quantifying the amount of inhibitor present in the sample based on the fluorescence measured in the sample compared to the fluorescence measured in a control sample containing only the RNAse and the circular supercoiled double-stranded plasmid;
characterized in that the fluorescence in the control sample is high due to the interconversion of the circular supercoiled double-stranded plasmid to a relaxed conformation in the presence of the RNAse; and
the fluorescence in the sample is lower than in the control sample if the sample contains an inhibitor of the RNAse.

8. The method, according to claim 7, comprising:
adding a circular supercoiled double-stranded plasmid comprising a nucleic acid sequence comprising an $(AT)_n$ sequence, characterized in that n is at least 12, the $(AT)_n$ sequence comprises at least one fluorophore and at least one quencher, each conjugated to a deoxythymidine (dT), and the fluorophore-conjugated dT and the quencher-conjugated dT are separated by at least 14 nucleotides and are located on the opposite DNA strand.

9. The method according to claim 7, comprising:
adding a circular supercoiled double-stranded plasmid comprising a nucleic acid sequence comprising an $(AT)_n$ sequence, characterized in that n is at least 12, the $(AT)_n$ sequence comprises at least one fluorophore and at least one quencher, each conjugated to a deoxythymidine (dT), and the fluorophore-conjugated dT and the quencher-conjugated dT are separated by 25 nucleotides and are located on the same DNA strand.

10. The method according to claim 7, comprising:
adding a circular supercoiled double-stranded plasmid comprising a nucleic acid sequence comprising an $(AT)_n$ sequence, characterized in that n is at least 12, the $(AT)_n$ sequence comprises at least one fluorophore and at least one quencher, each conjugated to a deoxythymidine (dT), and the fluorophore-conjugated dT and the quencher-conjugated dT are separated by 25 nucleotides and are located on the opposite DNA strand.

11. The method, according to claim 7, comprising:
adding a circular supercoiled double-stranded plasmid comprising a nucleic acid sequence comprising at least one RNA oligomer located on the opposite strand as the at least one fluorophore and the at least one quencher.

* * * * *